United States Patent [19]
Cabib et al.

[11] Patent Number: 5,912,165
[45] Date of Patent: *Jun. 15, 1999

[54] METHOD FOR CHROMOSOME CLASSIFICATION BY DECORRELAITON STATISTICAL ANALYSIS AND HARDWARE THEREFORE

[75] Inventors: Dario Cabib, Timrat; Robert A. Buckwald, Yishai; Nissim Ben-Yosef, Jerusalem, all of Israel

[73] Assignee: Applied Spectral Imaging Ltd, Migdal Haemek, Israel

[ * ] Notice: This patent is subject to a terminal disclaimer.

[21] Appl. No.: 08/942,549

[22] Filed: Oct. 1, 1997

Related U.S. Application Data

[62] Continuation of application No. 08/759,342, Dec. 2, 1996, Pat. No. 5,719,024, which is a continuation-in-part of application No. 08/718,831, filed as application No. PCT/US92/01171, Feb. 19, 1992, abandoned, which is a continuation-in-part of application No. 08/635,820, Apr. 22, 1996, Pat. No. 5,817,462, which is a continuation-in-part of application No. 08/575,191, Dec. 20, 1995, Pat. No. 5,831,732, which is a continuation-in-part of application No. 08/571,047, Dec. 12, 1995, Pat. No. 5,784,162, which is a continuation-in-part of application No. 08/392,019, Feb. 21, 1995, Pat. No. 5,539,517, which is a continuation-in-part of application No. 08/107,673, Aug. 18, 1993, abandoned.

[51] Int. Cl.$^6$ ............. C12M 1/34; G02B 21/16; F21V 9/08
[52] U.S. Cl. ............. 435/287.2; 359/368; 252/582
[58] Field of Search ............. 435/6, 287.2; 359/368; 252/582

[56] References Cited

U.S. PATENT DOCUMENTS 5,377,003  12/1994  Lewis et al. ............. 356/300
5,400,176  3/1995  Dreessen et al. ............. 359/385

OTHER PUBLICATIONS

Ploem "Fluorescence Microscopy" in Light Microscopy in biology; a practical approach Lacey Ed. IRL Press, 1989.

Reid et al. Simultaneous visualization of seven different DNA probes by in situ hybridization using combinatorial fluorescence and digital imaging microscopy. Proc. Natl. Acad. Sci. USA vol. 89 pp. 1388–1392, 1992.

*Primary Examiner*—George C. Elliott
*Assistant Examiner*—John S. Brusca
*Attorney, Agent, or Firm*—Mark M. Friedman

[57] ABSTRACT

A method and hardware for chromosome classification by decorrelation statistical analysis to provide color (spectral) karyotypes and to detect chromosomal aberrations. The method and hardware employ a set of N decorrelation matched filters for chromosome classification. The N decorrelation matched filters are dedicated for extracting decorrelated spectral data from chromosome samples painted according to a specific experimental protocol. The N decorrelation matched filters being described by:

$$F_{ik} = \frac{V_{ik} - V_{ik\,min}}{V_{ik\,max} - V_{ik\,min}}, k = 1\text{–}N$$

where $V_{ik\,min}$ equals minimum $V_{ik}$ over all i, and $V_{ik\,max}$ equals maximum $V_{ik}$ over all i, and wherein N is an integer greater than two.

14 Claims, 15 Drawing Sheets

METHOD FOR CHROMOSOME CLASSIFICATION BY DECORRELAITON STATISTICAL ANALYSIS AND HARDWARE THEREFORE

This is a continuation of U.S. patent application No. 08/759,342, filed Dec. 2, 1996, U.S. Pat. No. 5,719,024, which is a continuation-in-part of U.S. patent application No. 08/718,831, filed Sep. 24, 1996, now abandoned which is national stage of PCT/US92/01171 filed Feb. 19, 1992, which is a continuation-in-part of U.S. patent application No. 08/635,820, filed Apr. 22, 1996, U.S. Pat. No. 5,817,462, which is a continuation-in-part of U.S. patent application No. 08/575,191, filed Dec. 20, 1995, U.S. Pat. No. 5,831,732, which is a continuation-in-part of U.S. patent application No. 08/571,047, filed Dec. 12, 1995, U.S. Pat. No. 5,784,162, which is a continuation-in-part of U.S. patent application No. 08/392,019 filed Feb. 21, 1995, now U.S. Pat. No. 5,539,517, issued Jul. 23, 1996, which is a continuation-in-part of U.S. patent application No. 08/107,673, filed Aug. 18, 1993, now abandoned.

FIELD AND BACKGROUND OF THE INVENTION

The present invention relates to classification of in situ painted chromosomes into a color (spectral) karyotype. More particularly, the present invention relates to a method for classification of in situ painted chromosomes by decorrelation statistical analysis and hardware for such classification, the hardware is constructed according to parameters derived from the decorrelation statistical analysis.

The use of fluorescent dyes (i.e., fluorescent probes, fluorophores, fluorochromes, all are used interchangeably in this document), is one of the most powerful and common tools for analyzing tissues and cells. Fluorescence microscopy is therefore one of the most important experimental methods used in light microscopy [Lakowicz (1983) Principles of fluorescence spectroscopy, Plenum Press, New York, London].

The power of fluorescent probes, is mainly due to the great variety of biological structures to which specific dyes can be bound [Waggoner (1986) Applications of fluorescence in the biomedical sciences, Eds. Taylor et al., New York: Alan R. Liss, Inc. pp. 3–28]. For a detailed review of fluorescent probes see, Mason, editor (1993) Fluorescent and Luminescent Probes for Biological Activity, Biological Techniques Series, edited by Sattelle, Academic Press Limited, London; and, Ploem and Tanke (1987) Introduction to Fluorescence Microscopy, Oxford University Press, Royal Microscopical Society.

The rapid development of new and more sophisticated multicolor fluorescent dye molecules continues to create a need for more advanced fluorescence imaging techniques that can utilize the full potential of these dyes. For a discussion of the revolutionary impact fluorescent dyes have had, and will continue to have, on the way research is conducted today, refer to Taylor et al. (1992) The New Vision of Light Microscopy, American Scientist, Vol. 80, pp. 322–335.

An important example where the detection of multiple fluorescent probes can be a significant advantage is FISH (fluorescent in situ hybridization) [Emanuel (1993) Growth Genetics and Hormones 9, pp. 6–12], which is used to analyze genes at the chromosome level, and find possible genetic defects such as gene/chromosome amplification, deletion, translocation, rearrangement and other abnormalities.

Certain diseases and disorders, including many cancers and birth defects, are genetic disorders caused by defects (i.e., mutations) in one or more genes. Many other diseases are known or believed to have a genetic component(s), that is, there exists a genetic defect(s) that does not alone cause the disease but contributes to it, or increases the probability of developing the disease later in life, phenomena known in the art as multifactorial diseases and genetic predispositions.

Correlation of visible genetic defects with known diseases would allow doctors to make definitive diagnoses, and permit early detection and treatment of many diseases. Genetic counseling could alert prospective parents and at-risk individuals to the possibility of potentially serious medical problems in the future, permitting appropriate intervention.

More than 8,000 genetic disorders have now been identified, many of which are associated with multiple genetic defects. Following the discovery that chromosomes are the carriers of hereditary information, scientists reasoned that it should be possible to document visible defects in chromosomes that were responsible for specific disorders.

In the 1960's, staining techniques were developed for microscopy-based classification of metaphase chromosomes spread onto glass slides. For several decades, visual analysis of chromosomes banding patterns has been used to correlate human genetic disorders with observed structural abnormalities in metaphase chromosomes. Chromosomes are typically examined by brightfield microscopy after Giemsa staining (G-banding), or examined by fluorescence microscopy after fluorescence staining (R-banding), to reveal characteristic light and dark bands along their length. Careful comparison of a patient's banding pattern with those of normal chromosomes can reveal abnormalities such as translocations (exchange of genetic material between or within chromosomes), deletions (missing chromosome(s) or fragment(s) thereof), additions, inversions and other defects that cause deformities and genetic diseases. Yet conventional chromosome banding techniques are limited in resolution.

Fluorescent in situ hybridization (FISH) has evolved over the past 25 years through the improvement of a number of complementary techniques. Its emergence has been driven by the desire of cytogeneticists to develop better tools for mapping the precise location of genes on chromosomes, and to detect very small genetic defects not visible by gross staining of chromosomes.

The human genome project (HGP), a bold initiative to identify and map all human genes, has identified interest in FISH and has hastened the development of much-needed DNA probes. Current FISH techniques have also been made possible by the concurrent development of powerful immunological probes, a growing variety of excellent fluorescent dyes for microscopy and spectroscopy, and dramatic improvements in the objectives, illuminators and filters used for fluorescence microscopy.

The power and utility of FISH is due to many factors: (1) FISH can be used not only on isolated chromosomes and nucleus, but also whole cells within fixed, paraffin-embedded tissue sections; (2) it can detect relatively small defects (ability of detecting smaller defects constantly increases); (3) it can provide results relatively fast; (4) its moderate cost allows it to be used in most diagnostic and research laboratories; (5) adaptation can be developed for various probes and specimen types; and, (6) high specificity and sensitivity can be achieved; (7) within a short time, typically in the range two hours.

Many FISH applications merely require from the cytogeneticist to look through the eyepieces of a microscope, or at the image on the monitor, and to determine whether a fluorescent label is present or absent. With somewhat more complex specimens, a simple count of one or two colored labels may be done. However, the ability to process digital images and extract numerical data from them adds a vast new set of capabilities to FISH techniques.

An appropriate imaging method, can enhance very faint FISH images so that labeled chromosomes and loci are clearly identifiable. Under readily achieved experimental conditions, the number of labeled sites can be automatically counted. In addition, the intensity at each labeled site can be measured and the amount of DNA calculated to reveal, for example, the number of copies present of a particular gene.

As discussed above, FISH can provide information on the location of the labeled probe, the number of labeled sites on each chromosome, and the intensity of labeling (the amount of genetic material) at each site. Centromeric (repetitive DNA) probes and chromosome paints are used to tag and count the number of copies present of each targeted chromosome. Locus-specific probes are used to map the location of small regions of genetic material. These types of probes can be used on intact interphase nucleus as well as metaphase chromosome spreads, and can be counted visually or automatically by a suitable algorithm. They are routinely used to identify genetic diseases characterized by having too many or too few copies of a specific chromosome, chromosome fragment, or gene.

In very early stages of some cancers, long before the cells are recognized as abnormal, there may be an increase in the number of specific genes, phenomenon known in the art as gene amplification, that are detectable using locus-specific probes as homogeneously stained regions (HSR) and/or double minute chromosomes. Using FISH to detect chromosome abnormalities in cancerous cells may point out the developmental stage the disease has reached and therefore to select the most suitable treatment(s), many of which are stage specific in their effectiveness. Thereby precious time is saved and patient's suffering is minimized, selecting the most effective stage specific treatment.

It is possible to uniformly label the entire surface of one specific chromosome by isolating the chromosome (using flow cytometry, for example), physically (e.g., by sonication) or enzymatically (e.g., by endonucleases) chopping it up, and generating a set of probes against all of the fragments. Whole chromosome probes, also known as chromosome paints, fluorescently label all copies of their target chromosome. One important application of chromosome painting is the detection of translocation of genetic material between two chromosomes, as characteristically occurs in early stages of certain cancers, yet other chromosome aberrations are also detectable.

For example, if chromosome A is specifically labeled with a green paint and chromosome B is labeled with a red paint, any translocation of genetic material from A to B will appear as a green area on a red chromosome (and vice versa). Typically, chromosome paints generated from normal chromosomes are used to detect deletions or translocations on abnormal (patient) chromosomes. Reverse chromosome painting uses probes generated from an abnormal chromosome to identify DNA from various normal chromosomes which contributed material to the abnormal chromosome. The method of the present invention, as exemplified hereinbelow in the Examples section, enables to paint the 24 different chromosomes comprising the human karyotype (i.e., genome) each in a different color and simultaneously detect, identify and meaningfully display a color human karyotype, using a single hybridization followed by a single short measurement.

A remarked improvement in multicolor fluorescent dyes used for labeling chromosome paints is the introduction of combinatorial fluorescent strategies (e.g., combinatorial labeling and combinatorial hybridization) which employ various combinations of few basic fluorescent dyes. For further details on combinatorial labeling see, Ried et al., (1992) Simultaneous visualization of seven different DNA probes by in situ hybridization using combinatorial fluorescence and digital imaging microscopy. Proc. Natl. Acad. Sci. USA 89, 1388–1392; and, Ried (January 1994) Fluoreszenz in situ Hybridizierung in der genetischen Diagnostik, Faculty of theoretical medicine, Ruprecht-Karls University Heidelberg, both are incorporated by reference as if fully set forth herein. For further details about combinatorial hybridization see du-Manoir et al. (1993) Detection of complete and partial chromosome gains and losses by comparative genomic in situ hybridization. Hum. Genet. 90, 590–610, which is incorporated by reference as if fully set forth herein.

Numerous methods are available to label DNA probes for use in FISH assays, including indirect methods whereby a hapten such as biotin or digoxigenin is incorporated into DNA using enzymatic reactions. Following hybridization to a metaphase chromosome spread or interphase nucleus, a fluorescent label is attached to the hybrid through the use of immunological methods. More recently, fluorescent dyes have been directly incorporated into probes and detected without the use of an intermediate step. Standard FISH dyes include fluorescein, rhodamine, Texas-Red and cascade blue, and multiprobe FISH analysis can be accomplished by labeling different probes with different haptens or fluorescent dyes and combinations thereof, known in the art as combinatorial labeling [see, Ried et al., (1992) Simultaneous visualization of seven different DNA probes by in situ hybridization using combinatorial fluorescence and digital imaging microscopy. Proc. Natl. Acad. Sci. USA 89, 1388–1392; and, Ried (January 1994) Fluoreszenz in situ Hybridizierung in der genetischen Diagnostik, Faculty of theoretical medicine, Ruprecht-Karls University Heidelberg, both are incorporated by reference as if fully set forth herein]. Alternatively, a pool of a given probe may be divided into sub-pools, each labeled with a different fluorophore, after which the sub-pools are regrouped to yield otherwise similar hybridization results, a method known in the art as combinatorial hybridization [see, du-Manoir et al. (1993) Detection of complete and partial chromosome gains and losses by comparative genomic in situ hybridization. Hum. Genet. 90, 590–610, which is incorporated by reference as if fully set forth herein]. According to both labeling strategies obtained are combinatorial probes. Thus, when any of the terms "combination of fluorophores" or "combinatorial fluorescent strategy" is used herein in this document and especially in the claims below, it refers both to combinatorial labeling and to combinatorial hybridization as described above.

The use of combinatorial fluorophores for chromosome painting and karyotyping, multicolor chromosome banding and comparative genome hybridization is described in details in U.S. Pat. No. 5,817,462, and in Science magazine [E. Schroeck et al. (1996) Multicolor spectral karyotyping of human chromosomes. Science, 273, 494–497], both are incorporated by reference as if fully set forth herein.

The main progress described in Science is that whole genome scanning by spectral imaging allows instantaneous visualization of defined emission spectra for each human chromosome after fluorescence in situ hybridization (FISH). By means of computer separation (classification) of spectra, spectrally-overlapping chromosome-specific DNA probes are resolved and all human chromosomes are simultaneously identified.

This spectral imaging approach combines Fourier spectroscopy, charge coupled device (CCD)-imaging, and optical microscopy to measure simultaneously at all points in the sample emission spectra in the visible and near-infrared spectral range. This allows the use of multiple spectrally overlapping probes. The approach is based on the measurement of a discrete spectrum (identified from a sequence of intensities at every pixel measured at many different wavelengths), which facilitates the discrimination of multiple fluorophores. In dramatic contrast to conventional epifluorescence microscopy in which fluorochrome discrimination is based on the measurement of a single intensity through a fluorochrome specific optical filter [see, Speicher et al. (1996) Nature Genetics. 12:368–375], the use of spectral karyotyping allows all information within the spectrum of emitted light to be used for analysis.

The spectral-based method for discriminating spectrally overlapping fluorophores (classification) is readily extended to a large number of fluorochromes, provided there are measurable and consistent differences in the emission spectrum of each fluorochrome.

Simultaneous identification of each human chromosome in metaphase preparations, an approach referred to as spectral karyotyping, is also reported. To this end, chromosome-specific composite libraries generated by polymerase chain reaction (PCR) from flow-sorted human chromosomes are directly labeled with nucleotides conjugated to five different fluorophores or combinations thereof. A composite probe set containing all 24 chromosomes is then hybridized to metaphase chromosomes. Chromosome-specific labeling is achieved by suppression hybridization. Specifically, repetitive sequences in the composite libraries are blocked by the addition of an excess of unlabeled human Cot-1 DNA.

The hybridization is presented in both RGB display and classification colors. Display colors allow all human chromosomes to be readily visualized after spectral imaging, and based on spectral measurements at each pixel, a chromosome classification algorithm is applied to spectrally karyotype all human chromosomes. One of the most important analysis algorithms is the spectral-based classification algorithm that enables multiple different spectra in the image to be identified and highlighted in classification-colors. This allows assignment of a specific classification-color to all human chromosomes based on their spectra. This algorithm assumes that the (reference) spectrum of each chromosome has been measured and stored in a reference library in the computer. A classification-color is assigned to each pixel in the image according to the classification-color assigned to the reference spectrum that is most similar to the spectrum at that given pixel. A minimal square error algorithm as shown in Equation 1:

$$S_{x,y,n} = \int_{\lambda 1}^{\lambda 2} (I_{x,y}(\lambda) - I_n(\lambda))^2 \, d\lambda \quad (1)$$

is computed for every pixel, in which $I_{x,y}(\lambda)$ is the normalized spectrum at pixel coordinates x,y and $I_n(\lambda)$ represents the normalized reference spectrum for each of the chromosome n=1, 2, . . . , 23, 24. After calculating the value of $S_{x,y,n}$ for all reference spectra, the smallest value is chosen and an artificial classification-color is assigned to that pixel in accordance with the classification-color assigned to the most similar reference spectrum.

The potential of spectral karyotyping as a screening method for chromosomal aberrations was further explored by analyzing clinical samples from multiple laboratories where conventional banding methods or FISH with chromosome painting probes had been previously performed. In all cases, G-banding and spectral karyotyping revealed consistent results. In some cases, Giemsa-banding was not sufficient to entirely interpret the chromosomal aberrations. In these cases, the diagnosis of chromosomal aberrations by spectral karyotyping was confirmed with conventional dual-color FISH analysis. The smallest discernible aberration analyzed for this report was a translocation t(1;11) (q44;p15.3) in which the reciprocal translocation was unrecognizable by conventional banding analysis. The origin of the chromosomal material that contributed to the reciprocal translocation was correctly classified. The translocated segments on chromosomes 1 and 11 had been confirmed by subtelomere specific cosmid probes for chromosomes 1q and 11p. On the basis of the location of the probes utilized, the size of the alteration was estimated to be >1,500 kbp. In a second case, banding analysis suggested a translocation of a segment of chromosome 4 to chromosome 12. Spectral karyotyping unambiguously identified and classified the origin of the additional chromosomal material as being derived from chromosome 4. To determine the limit of sensitivity of spectral karyotyping, a case with a submicroscopic translocation (unrecognizable in both metaphase and prometaphase chromosomes) involving chromosomes 16 and 17 was examined. This t(16;17) had been previously demonstrated by FISH with cosmid probes and the reciprocal interchange of chromatin estimated at approximately 500 kbp. Spectral karyotyping with metaphase chromosomes from this patient failed to identify the known t(16;17) suggesting that the limit of sensitivity for metaphase chromosome analysis with currently available painting probes to be between 500–1,500 kbp.

To demonstrate that spectral karyotyping is an approach that can be used to complement conventional banding analysis, hybridization on previously G-banded chromosomes was performed. Probably due to the trypsin digestion that is required for G-banding, the signal intensity was slightly reduced as compared to metaphases that were not previously G-banded. The loss of signal intensity was approximately 10%, and could therefore easily be compensated for by prolonged exposure times. A slightly increased noise at the edges of previously G-banded chromosomes compared to non G-banded chromosomes was also observed. However, the classification of the metaphase could be readily achieved.

Yet, the method disclosed in Science magazine and described above has limitations. A spectral image composed of 300×300 pixels and fifty wavelengths for each spectrum is a file of Ca. 4.5 Megabytes. In the system described in Science the interferogram for each pixel contains at least double number of data, Ca. 9.0 Megabytes for each measurement, before the Fourier Transform is calculated. This is a large amount of data, which takes a long time to collect and occupies a large amount of memory to store.

The present invention is directed at providing a system (hardware and software) which performs a measurement, with higher sensitivity and at higher speed, and encompassing a much smaller amount of data from the outset. The hardware does not require an interferometer, but only a number (N) of what is herein referred to as "decorrelation matched filters", which are placed in the path of the incoming light beam from the object to be measured. The filters may be of a fixed nature or tunable (AOTF or LCTF). In the later case a single tunable filter is used to sequentially implement the decorrelation matched filters under electronic control. The filters are matched to take advantage of the correlations between the spectral data derived from chromosomes painted using a given experimental protocol, only to which protocol the filters match for best results: these results are (i) increased signal to noise ratio due to averaging between the correlated data, and (ii) reduction of the amount of data and measurement time needed at the outset, due to the projection of the spectra onto a decorrelated parameter space. As is described below in detail, the number of filters required to achieve a good measurement is much lower than the number of wavelengths of the original spectral image so that the measurement itself is much shorter.

SUMMARY OF THE INVENTION

According to the present invention there is provided a method and hardware for chromosome classification by decorrelation statistical analysis which can be used to provide color (spectral) karyotypes and to detect chromosomal aberrations.

According to further features in preferred embodiments of the invention described below, provided is a method for preparing a reference template for chromosome classification, the method comprising the steps of (a) obtaining at least one sample of a complete set of metaphase chromosomes of a species having L types of chromosomes, the chromosomes of each of the at least one sample being preclassified via a conventional chromosome classification technique; (b) painting the chromosomes of each of the at least one samples with L different fluorophores-or-combinations-of-fluorophores, such that chromosomes which belong to each of the L types are differently painted; (c) using a spectral imager to measure a spectral cube for each of the at least one samples, such that at least one spectral cube is obtained; (d) employing a decorrelation statistical method to extract decorrelated spectral data characterizing each of the L types of preclassified chromosomes; and (e) using at least a part of the decorrelated spectral data for the preparation of the reference template for chromosome classification.

According to still further features in the described preferred embodiments the decorrelation statistical method is principal component analysis, canonical variable analysis or singular value decomposition, etc.

According to still further features in the described preferred embodiments the principal component analysis includes the steps of (a) selecting k spectral slices for each spectral cube of each of the at least one samples; (b) calculating an average spectrum for each of the chromosomes; (c) stretching each of the average spectra for obtaining a stretched average spectrum for each of the chromosomes; (d) averaging the stretched average spectra for each of the L chromosome types for obtaining an ensemble average spectrum for each of the L types of chromosomes; (e) calculating a k dimension eigen system for the L ensemble average spectra and extracting N eigenvectors (k>N); (f) using the N eigenvectors for defining an N-dimension vector for each of the L chromosome types; and (g) using the L N-dimension vectors for preparing the reference template for chromosome classification.

According to still further features in the described preferred embodiments the principal component analysis further includes (h) performing a spatial averaging procedure on all spectral slices; and (i) performing a background subtraction procedure;

According to still further features in the described preferred embodiments provided is a method for chromosome classification employing the reference template as described above, the method comprising the steps of (a) obtaining a sample of chromosomes of a species having L types of chromosomes; (b) painting the chromosomes with L different fluorophores-or-combinations-of-fluorophores, such that chromosomes which belong to each of the L types are differently painted; (c) using a spectral imager to measure a spectral cube for the sample, such that a spectrum of each pixel in the sample is obtained; (d) employing a decorrelation statistical method to extract decorrelated spectral data characterizing each of the pixels; and (e) comparing at least a part of the decorrelated spectral data with the reference template.

According to still further features in the described preferred embodiments the method for chromosome classification further comprising the step of (f) according to the comparison, attributing each pixel an artificial color selected from L different types of colors.

According to still further features in the described preferred embodiments provided is a method for chromosome classification employing the reference template as described above, the method comprising the steps of (a) obtaining a sample of chromosomes of a species having L types of chromosomes; (b) painting the chromosomes with L different fluorophores-or-combinations-of-fluorophores, such that chromosomes which belong to each of the L types are differently painted; (c) using a spectral imager to measure a spectral cube for the sample, such that a spectrum of each pixel in the sample is obtained; (d) projecting the spectrum of each of the pixels into the N decorrelated eigenvectors for obtaining a projected N dimension vector for each of the pixels; and (e) correlating each of the N dimension vectors with the reference template.

According to still further features in the described preferred embodiments the method for chromosome classification further comprising the steps of (h) performing a spatial averaging procedure on all spectral slices; and (i) performing a background subtraction procedure.

According to still further features in the described preferred embodiments provided is a method of calculating decorrelation matched filters for chromosome classification employing the reference template (N eigenvectors) as described above, the decorrelation matched filters being for extracting decorrelated spectral data from chromosome samples painted according to a specific experimental protocol, the method comprising the step of mathematically manipulating the at least part of the decorrelated spectral data for obtaining a mathematical description of the decorrelation matched filters.

According to still further features in the described preferred embodiments provided is a method for chromosome classification employing the reference template as described above, the method comprising the steps of (a) obtaining a sample of chromosomes of a species having L types of chromosomes; (b) painting the chromosomes with L different fluorophores-or-combinations-of-fluorophores, such that chromosomes which belong to each of the L types are differently painted; (c) calculating a mathematical description of decorrelation matched filters for chromosome classification employing the reference template, the calculation being by mathematically manipulating the at least part of the decorrelated spectral data; (d) using the mathematical description of the decorrelation matched filters for manufacturing the decorrelation matched filters; (e) using the decorrelation matched filters for extracting decorrelated spectral data from each pixel of the chromosomes sample; and (f) comparing the decorrelated spectral data with the reference template.

According to still further features in the described preferred embodiments the method for chromosome classification further comprising the step of (g) attributing each pixel an artificial color selected from L different types of colors, according to the comparison.

According to still further features in the described preferred embodiments provided is a set of decorrelation matched filters for chromosome classification, the decorrelation matched filters being for extracting decorrelated spectral data from chromosome samples painted according to a specific experimental protocol, the set of decorrelation matched filters is manufactured according to the mathematical description as described above.

According to still further features in the described preferred embodiments provided is a set of information for implementing decorrelation matched filters for chromosome classification via a tunable filter, the implemented decorrelation matched filters being for extracting decorrelated spectral data from chromosome samples painted according to a specific experimental protocol, the set of information is calculated according to the mathematical description as described above.

According to still further features in the described preferred embodiments the tunable filter is selected from the group consisting of AOTF and LCTF.

According to still further features in the described preferred embodiments provided is a method for chromosome classification employing the decorrelation matched filters for chromosome classification as described above, the method comprising the steps of (a) obtaining a sample of chromosomes of a species having L types of chromosomes; (b) painting the chromosomes with L different fluorophores-or-combinations-of-fluorophores, such that chromosomes which belong to each of the L types are differently painted; (c) using the decorrelation matched filters for extracting decorrelated spectral data from each pixel of the chromosomes sample; and (d) comparing the decorrelated spectral data with the reference template.

According to still further features in the described preferred embodiments the method for chromosome classification further comprising the step of (e) according to the comparison, attributing each pixel an artificial color selected from L different types of colors.

According to still further features in the described preferred embodiments provided is a method for chromosome classification employing the information for implementing decorrelation matched filters for chromosome classification as described above, the method comprising the steps of (a) obtaining a sample of chromosomes of a species having L types of chromosomes; (b) painting the chromosomes with L different fluorophores-or-combinations-of-fluorophores, such that chromosomes which belong to each of the L types are differently painted; (c) using the information for implementing decorrelation matched filters by the tunable filter for extracting decorrelated spectral data from each pixel of the chromosomes sample; and (d) comparing the decorrelated spectral data with the reference template.

According to still further features in the described preferred embodiments provided is a spectral decorrelation measurement apparatus for chromosome classification by extracting decorrelated spectral data from a chromosome sample painted according to a specific experimental protocol, the apparatus is connected to a microscope used to view the sample, the apparatus comprising (a) a light source; (b) a detector; and (c) an optical system for transmitting excitation light from the light source onto the sample and emission light from the sample onto the detector, the optical system including a set of decorrelating matched filters, the decorrelation matched filters being for extracting decorrelated spectral data from the chromosome sample painted according to the specific experimental protocol, the set of decorrelation matched filters being manufactured according to the mathematical description of as described above.

According to still further features in the described preferred embodiments the optical system further includes (i) an excitation filter placed in the path of light emitted from the light source for transmitting light in the range required for excitation of fluorophores contained in the sample and for blocking light in the range of emission; (ii) a dichroic filter for directing exiting light from the filter to the sample and emission light from the sample to the detector; and (iii) a focusing lens for focusing emitted light onto the detector.

According to still further features in the described preferred embodiments the optical system further includes (iv) a barrier filter for blocking any residual photons which are not in the spectral range of emission.

According to still further features in the described preferred embodiments the optical system further includes (iv) a collimating lens for collimating light reaching to any of the decorrelating matched filters.

According to still further features in the described preferred embodiments the decorrelation matched filters are arranged on a rotatable filter carrying element.

According to still further features in the described preferred embodiments provided is a spectral decorrelation measurement apparatus for chromosome classification by extracting decorrelated spectral data from a chromosome sample painted according to a specific experimental protocol, the apparatus is connected to a microscope used to view the sample, the apparatus comprising (a) a light source; (b) a detector; and (c) an optical system for transmitting excitation light from the light source onto the sample and emission light from the sample onto the detector, the optical system including a tunable filter and a tuning device, the tuning device being for tuning the tunable filter to sequentially implement a set of decorrelating matched filters, the sequentially implemented decorrelation matched filters being for extracting decorrelated spectral data from the chromosome sample painted according to the specific experimental protocol, the tuning of the tunable filter being calculated according to the mathematical description of claim as described above.

According to still further features in the described preferred embodiments provided is a method for preparing a reference template for chromosome banding analysis, the method comprising the steps of (a) obtaining at least one sample of a complete set of metaphase chromosomes of a species having L types of chromosomes, the chromosomes of each of the at least one sample being preclassified via a conventional chromosome classification technique; (b) painting the chromosomes of each of the at least one samples with different fluorophores-or-combinations-of-fluorophores, such that fragments of each of the L chromosome types are differently painted; (c) using a spectral imager to measure a spectral cube for each of the at least one samples, such that at least one spectral cube is obtained; (d)

employing a decorrelation statistical method to extract decorrelated spectral data characterizing each of the fragments of preclassified chromosomes; and (e) using at least a part of the decorrelated spectral data for the preparation of the reference template for chromosome banding analysis.

According to still further features in the described preferred embodiments the decorrelation statistical method is selected from the group consisting of principal component analysis, canonical variable analysis and singular value decomposition.

According to still further features in the described preferred embodiments the principal component analysis includes expressing each of the fragments as linear combinations of N eigenvectors.

According to still further features in the described preferred embodiments the principal component analysis includes the steps of (a) selecting k spectral slices for each spectral cube of each of the at least one samples; (b) calculating an average spectrum for each of the fragments; (c) stretching each of the average spectra for obtaining a stretched average spectrum for each of the fragments; (d) averaging the stretched average spectra for each of the fragments for obtaining an ensemble average spectrum for each of the fragments; (e) calculating a k dimension eigen system for the ensemble average spectra and extracting N eigenvectors; (f) using the N eigenvectors for defining an N-dimension vector for each of fragments; and (g) using the N-dimension vectors for preparing the reference template for chromosome banding analysis.

According to still further features in the described preferred embodiments the principal component analysis further includes (h) performing a spatial averaging procedure on all spectral slices; and (i) performing a background subtraction procedure;

According to still further features in the described preferred embodiments provided is a method for chromosome banding analysis employing the reference template for chromosome banding as described above, the method comprising the steps of (a) obtaining a sample of chromosomes of a species having L types of chromosomes; (b) painting the chromosomes with different fluorophores-or-combinations-of-fluorophores, such that fragments of each of the L chromosome types are differently painted; (c) using a spectral imager to measure a spectral cube for the sample, such that a spectrum of each pixel in the sample is obtained; (d) employing a decorrelation statistical method to extract decorrelated spectral data characterizing each of the pixels; and (e) comparing at least a part of the decorrelated spectral data with the reference template.

According to still further features in the described preferred embodiments provided is a method for chromosome banding analysis employing the reference template for chromosome banding as described above, the method comprising the steps of (a) obtaining a sample of chromosomes of a species having L types of chromosomes; (b) painting the chromosomes with different fluorophores-or-combinations-of-fluorophores, such that fragments of each of the L chromosome types are differently painted; (c) using a spectral imager to measure a spectral cube for the sample, such that a spectrum of each pixel in the sample is obtained; (d) projecting the spectrum of each of the pixels onto the decorrelated spectral data for obtaining a projected spectrum for each of the pixels; and (e) comparing the projected spectra with the reference template.

According to still further features in the described preferred embodiments the method for chromosome banding analysis further comprising the step of (f) according to the comparison, attributing each pixel an artificial color.

According to still further features in the described preferred embodiments provided is a method for chromosome banding analysis employing the reference template for chromosome banding as described above, the method comprising the steps of (a) obtaining a sample of chromosomes of a species having L types of chromosomes; (b) painting the chromosomes with different fluorophores-or-combinations-of-fluorophores, such that fragments of each of the L chromosome types are differently painted; (c) using a spectral imager to measure a spectral cube for the sample, such that a spectrum of each pixel in the sample is obtained; (d) projecting the spectrum of each of the pixels into the N eigenvectors for obtaining a projected N dimension vector for each of the pixels; and (e) correlating each of the projected N dimension vectors with the reference template.

According to still further features in the described preferred embodiments the method further comprising the steps of (h) performing a spatial averaging procedure on all spectral slices; and (i) performing a background subtraction procedure.

According to still further features in the described preferred embodiments provided is a method of calculating decorrelation matched filters for chromosome banding analysis employing the reference template for chromosome banding as described above, the decorrelation matched filters being for extracting decorrelated spectral data from chromosome samples painted according to a specific chromosome banding experimental protocol, the method comprising the step of mathematically manipulating the at least part of the decorrelated spectral data for obtaining a mathematical description of the decorrelation matched filters.

According to still further features in the described preferred embodiments the decorrelated spectral data is obtained using a principal component analysis which includes expressing each of the chromosome fragments by a linear combination of N eigenvectors.

According to still further features in the described preferred embodiments provided is a set of decorrelation matched filters for chromosome banding analysis, the decorrelation matched filters being for extracting decorrelated spectral data from chromosome samples painted according to a specific experimental banding protocol, the set of decorrelation matched filters is manufactured according to the mathematical description described above.

According to still further features in the described preferred embodiments provided is a set of information for implementing decorrelation matched filters for chromosome banding analysis via a tunable filter, the decorrelation matched filters being for extracting decorrelated spectral data from chromosome samples painted according to a specific experimental banding protocol, the set of information is calculated according to the mathematical description as described above. Preferably the tunable filter is selected from the group consisting of AOTF and LCTF.

According to still further features in the described preferred embodiments provided is a method for chromosome banding analysis employing the reference template for chromosome banding as described above, the method comprising the steps of (a) obtaining a sample of chromosomes of a species having L types of chromosomes; (b) painting the chromosomes with different fluorophores-or-combinations-of-fluorophores, such that fragments of each of the L chromosome types are differently painted; (c) calculating a mathematical description of decorrelation matched filters for chromosome banding analysis employing the reference template, the calculation being by mathematically manipulating the at least part of the decorrelated spectral data; (d) using the mathematical description of the decorrelation matched filters for manufacturing the decorrelation matched filters; (e) using the decorrelation matched filters for extracting decorrelated spectral data from each pixel of the chromosomes sample; and (f) comparing the decorrelated spectral data with the reference template.

According to still further features in the described preferred embodiments the method further comprising the step of (g) attributing each pixel an artificial color according to the comparison.

According to still further features in the described preferred embodiments provided is a method for chromosome banding analysis employing the decorrelation matched filters for chromosome banding analysis as described above, the method comprising the steps of (a) obtaining a sample of chromosomes of a species having L types of chromosomes; (b) painting the chromosomes with different fluorophores-or-combinations-of-fluorophores, such that fragments of each of the L chromosome types are differently painted; (c) using the decorrelation matched filters for extracting decorrelated spectral data from each pixel of the chromosomes sample; and (d) comparing the decorrelated spectral data with the reference template.

According to still further features in the described preferred embodiments the method further comprising the step of (e) according to the comparison, attributing each pixel an artificial color.

According to still further features in the described preferred embodiments provided is a method for chromosome banding analysis employing the information for implementing decorrelation matched filters for chromosome banding analysis as described above, the method comprising the steps of (a) obtaining a sample of chromosomes of a species having L types of chromosomes; (b) painting the chromosomes with different fluorophores-or-combinations-of-fluorophores, such that fragments of each of the L chromosome types are differently painted; (c) using the information for implementing decorrelation matched filters by the tunable filter for extracting decorrelated spectral data from each pixel of the chromosomes sample; and (d) comparing the decorrelated spectral data with the reference template.

According to still further features in the described preferred embodiments provided is a spectral decorrelation measurement apparatus for chromosome banding analysis by extracting decorrelated spectral data from a chromosome sample painted according to a specific experimental banding protocol, the apparatus is connected to a microscope used to view the sample, the apparatus comprising (a) a light source; (b) a detector; and (c) an optical system for transmitting excitation light from the light source onto the sample and emission light from the sample onto the detector, the optical system including a set of decorrelating matched filters, the decorrelation matched filters being for extracting decorrelated spectral data from the chromosome sample painted according to the specific experimental banding protocol, the set of decorrelation matched filters being manufactured according to the mathematical description described above.

According to still further features in the described preferred embodiments provided is a spectral decorrelation measurement apparatus for chromosome banding analysis by extracting decorrelated spectral data from a chromosome sample painted according to a specific experimental banding protocol, the apparatus is connected to a microscope used to view the sample, the apparatus comprising (a) a light source; (b) a detector; and (c) an optical system for transmitting excitation light from the light source onto the sample and emission light from the sample onto the detector, the optical system including a tunable filter and a tuning device, the tuning device being for tuning the tunable filter to sequentially implement a set of decorrelating matched filters, the sequentially implemented decorrelation matched filters being for extracting decorrelated spectral data from the chromosome sample painted according to the specific experimental protocol, the tuning of the tunable filter being calculated according to the mathematical description as described above.

According to still further features in the described preferred embodiments the species is human and L equals 24.

According to still further features in the described preferred embodiments the painting is by combinatorial fluorescent strategy is combinatorial labeling or combinatorial hybridization.

According to still further features in the described preferred embodiments the decorrelation statistical method is principal component analysis, canonical variable analysis or singular value decomposition, etc.

According to still further features in the described preferred embodiments k is an integer greater than nine, k is preferably selected between 9 and 21, yet larger values for k are also possible.

According to still further features in the described preferred embodiments the principal component analysis includes expressing each of the L types of chromosomes as linear combinations of N eigenvectors.

According to still further features in the described preferred embodiments N is an integer greater than two.

According to still further features in the described preferred embodiments N is an integer greater than two and smaller than eight.

According to still further features in the described preferred embodiments the chromosomes are metaphase chromosomes, interphase chromosomes or chromosomes undergoing meiosis.

According to still further features in the described preferred embodiments the chromosomes are of a fetal cell, a cancerous cell or an adult healthy cell.

According to still further features in the described preferred embodiments the chromosomes are of a solid tumor cell or a blood tumor cell.

The present invention successfully addresses the shortcomings of the presently known configurations by providing a system (hardware and software) which performs a measurement, with higher sensitivity and at higher speed, and encompassing a much smaller amount of data from the outset. The hardware does not require an interferometer, but only a number (N) of what is herein referred to as "decorrelation matched filters", which are placed in the path of the incoming light beam from the object to be measured. The filters may be of a fixed nature or tunable (AOTF or LCTF). In the later case a single tunable filter is used to sequentially implement the decorrelation matched filters under electronic control. The filters are matched to take advantage of the correlations between the spectral data derived from chromosomes painted using a given experimental protocol, only to which protocol the filters match for best results which include (i) increased signal to noise ratio due to averaging between the correlated data, and (ii) reduction of the amount of data and measurement time needed at the outset, due to the projection of the spectra onto a decorrelated parameter space. As is described below in detail, the number of filters required to achieve a good measurement is much lower than the number of wavelengths of the original spectral image so that the measurement itself is much shorter.

It is an object of the present invention to provide a method and system for analysis of chromosomes.

It is another object of the present invention to provide a method and system for quick detection of chromosomal aberrations.

It is yet another object of the present invention to provide a method and system providing a color karyotype.

It is still another object of the present invention to provide a method and system which can accomplish the above objectives invention with high signal to noise ratio and in a short time, by employing decorrelation statistical analysis when implementing the method and when constructing the system.

These and other objectives of the invention are further detailed below.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

The invention herein described, by way of example only, with reference to the accompanying drawings, wherein.

DESCRIPTION OF THE PREFERRED EMBODIMENTS

Figure 1:
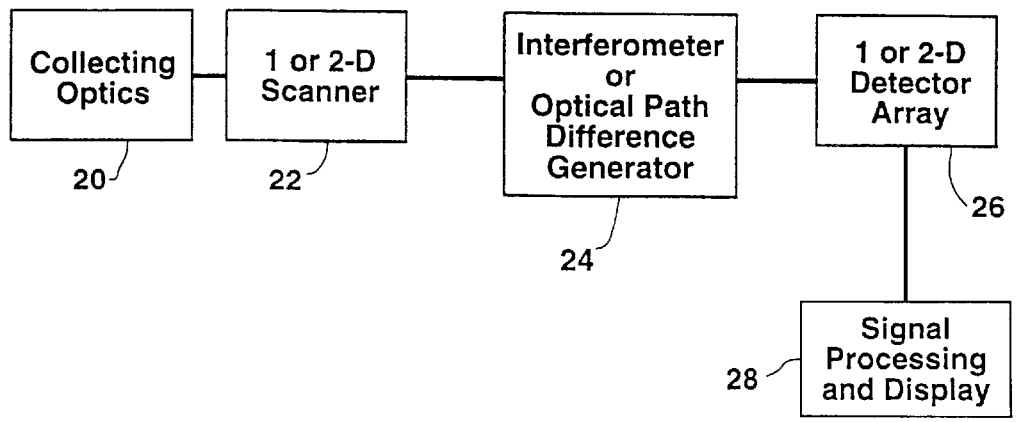
FIG. 1 is a block diagram illustrating the main components of an imaging spectrometer constructed in accordance with U.S. Pat. No. 5,539,517 (prior art)

The present invention is of a method and hardware for chromosome classification by decorrelation statistical analysis which can be used to provide color (spectral) karyotypes and to detect chromosomal aberrations. Specifically, the present invention can be used to design decorrelation matched optical filters, also referred herein as "matched" filters, for fast measurement aimed at chromosome classification, karyotyping and the detection of chromosomal aberrations.

The principles and operation of the method and decorrelation matched filters according to the present invention may be better understood with reference to the drawings and accompanying descriptions.

Spectral imaging is the technology that enables the measurement of the spectrum of light emitted by every point (pixel) of an object. A spectral imager (also referred herein as imaging spectrometer) is an instrument that measures and stores in memory for later retrieval and analysis the spectrum of light emitted by every point of the object which is placed in its field of view. A spectral image is a collection of spectra of the object measured by a spectral imager. It is usually organized as an intensity function defined in a three dimensional space in which two dimensions are of an image (x and y), and one is of a spectral axis ($\lambda$). As such, a spectral image is usually referred to as a "cube" of data or "spectral cube".

Prior art teaches different methods of measuring spectral images (i.e., spectral cubes). Devices designed according to these methods include light collection optics; a dispersion element (e.g., a grating), filter(s) (e.g., AOTF or LCTF) or an interferometer; focusing optics; and a two-dimensional array of detectors (typically a CCD in the visible range and other types of detectors in the infrared range).

Each method has advantages and disadvantages, however as shown in U.S. Pat. No. 5,539,517 to Cabib et al., filed Feb. 21, 1995, and in Journal of Microscopy [Vol. 182, pp.133–140, 1996], both are incorporated by reference as if fully set forth herein, a spectral imager based on a special type of triangular interferometer has advantages of compactness and stability that more conventional spectral imagers do not have. A spectral imager in accordance with the invention disclosed in U.S. Pat. No. 5,539,517 was developed by Applied Spectral Imaging Ltd., Industrial Park, Migdal Haemek, Israel and is referred hereinbelow as SpectraCube™.

The importance of a spectral image measurement resides in the fact that the spectrum of light carries information about the composition of matter of which the object is made, and therefore it can be used to map and visualize phenomena which cannot be seen otherwise. As a color image is the next step after a black and white image, a spectral image is the next step after a color image. Similarly to the difference of green hues between the leaves of two different types of trees or between a young leaf and an old one, two fluorescent dyes such as Texas Red and Rhodamine appear the same color to the human eye but they are well distinguished by a spectrograph with ten nanometers resolution. A complex biological system such as a white blood cell stained with Giemsa, looks to the eye through the microscope in transmission of white light, as an object with structures composed of regions of purple, blue and reddish colors in different levels of intensity. Since the colors as perceived by the human eye are composed of combinations of only three colors, red, green and blue (RGB), the number of different regions in the cell that can be classified by color is very limited. For each point of the same cell a spectral imager measures a spectrum which depends on the chemical materials present at that point, and this is a function of wavelength which contains the order of fifty or one hundred data (depending on spectral resolution) instead of only three as for a color image. As a result, small spectral differences or shifts between pixels can be detected by a spectral imager, which the eye would recognize as belonging to the same color class, and therefore many more classes of biological structures or components can be distinguished in the cell using a spectral imager, as compared with the human eye.

For example, in Fluorescence Imaging Spectroscopy and Microscopy, edited by X. F. Wang and B. Herman, Vol. 137 pp. 87–124, 1996, John Wiley & Sons, a nuclear wall is shown sharply distinct by the rest of the nucleus in a spectral image, contrary to a simple color image where the wall is perceived as part of the nucleus (see ibidem FIG. 4.10d on age 115).

In E. Schroeck et al. (1996) Multicolor spectral karyotyping of human chromosomes. Science, 273, 494–497, it is shown how a spectral imager as disclosed in U.S. Pat. No. 5,539,517 is used in combination with fluorescence in situ hybridization (FISH) techniques to analyze combinatorially painted chromosomes (human and animals), so that karyotyping and chromosomal aberrations can be easily and reliably characterized.

According to this technique each chromosome is hybridized with complementary DNA material which contains a different combination of fluorescent dyes out of a larger set of dyes, such that each chromosome of a metaphase spread emits a different fluorescence spectrum uniformly over its surface. Typically, each chromosome is labeled with a different combination of up to three dyes (e.g., one, two or three dyes) selected from a set of five dyes, resulting in 24 different fluorescence spectra, one for each chromosome. This is done with human (requiring 24 different spectra or 24 combinations of dyes), mouse and monkey chromosomes (for which the number is different than 24), and with healthy and diseased (e.g., cancerous) cells. The detection and identification of translocations while using this method is immediate and reliable because the different spectrum of a translocation stands out clearly in the surrounding chromosome, whereas the information carried by the G-banding technique widely used today is much less obvious for this purpose.

A spectral image composed of 300×300 pixels and fifty wavelengths for each spectrum is a file of Ca. 4.5 Megabytes. In the system described in U.S. Pat. No. 5,539,517 the interferogram for each pixel contains at least double number of data, Ca. 9.0 Megabytes for each measurement, before the Fourier transform is calculated. This is a large amount of data, which takes a long time to collect and occupies a large amount of memory to store.

The present invention is aimed at constructing a system which performs the same measurement, with higher sensitivity, and at higher speed, and encompassing a much smaller amount of data from the outset. The hardware according to the invention does not require an interferometer, but only a number (N) of what is herein referred to as "decorrelation matched filters" (fixed or tunable), which are designed using decorrelating statistical analysis such as principal component analysis (PCA) and are placed in the path of the incoming light beam from the object to be measured.

It turns out that the number of filters (or their implementations by a tunable filter) required to achieve a good measurement is much lower than the number of wavelengths of the original spectral image. Furthermore, because there are correlations between the spectral data at different wavelengths, therefore a measurement collected by the hardware according to the invention is much shorter.

The basis for this new concept is the realization that out of fifty data points (or a similar large number) corresponding to fifty wavelengths for a spectrum in the range of Ca. 500 to 750 nanometers, there usually are much less than fifty decorrelated data. Decorrelation enables to decrease the amount of data taking at the outset, while the correlations among the data are taken advantage of in order to increase the signal to noise ratio. Thus when the term 'decorrelation' is used herein in this document and especially in the claims section below, it refers to an algorithm which defines an initial set of correlated parameters into a new set of parameters which is the linear combination of the initial set, which new set of parameters are independent from each other and are then reduced to a minimal number which still carries the required information.

A classification method based on the position of an object in a multidimensional space defined by a decorrelated set of parameters is characterized by increased confidence level and shorter measurement time as compared with classification methods employing the initial set of parameters devoid of prior decorrelation.

Each decorrelation matched filter is mathematically described by a weighting function whose shape is such that the parameters which are more correlated are added with a larger weight. Different filters, in order to decorrelate the data, have a different shape and therefore weigh the initial parameters values in different ways. However, the signal obtained using each of the filters has contribution from all initial parameters, therefore the signal is measured with higher signal to noise ratio as compared with other, more conventional, methods.

The decorrelation matched filters are dedicated for a given experimental procedure in which the dyes and their combinations as applied to any chromosome are predetermined. Changing the dyes and/or combinations, in most cases will require a complete new set of decorrelation matched filters. This feature of the decorrelation matched filters according to the invention is further emphasized hereinbelow.

Nevertheless, should tunable filters such as LCTF and AOTF be used to implement the set of decorrelation matched filters, appropriate tuning, as is further described hereinbelow, can be used to acquire an implementation of the new set of decorrelation matched filters As will be described in greater detail below, in one embodiment of the invention the decorrelation matched filters are placed in a filter wheel of the dedicated hardware according to the invention and are introduced successively in the beam, while a CCD builds the images. That is to say that the CCD builds an image with one filter, then the wheel rotates to another filter, and the CCD builds a new image in synchronization, and so on until one image for each filter has been measured (N images).

As will be further described below, in another embodiment of the invention the decorrelation matched filters are implemented by tunable filters such as AOTF and LCTF which are tuned by a tuning device. At successive times the tuning device tunes the tunable filter to implement one of the N different decorrelation matched filters and the CCD builds an image for each of the N implementations.

In both cases, for each pixel in the object a vector of dimensionality N is obtained. The elements of this vector are the intensities for that particular pixel, measured through each one of the N filters, and they vary according to which one of the dye combinations is present in that pixel, which in turn corresponds to one and only one chromosome. Each pixel is then classified as belonging to that particular chromosome.

Thus, according to the present invention provided is a method and hardware for chromosome classification by decorrelation statistical analysis which can be used to provide color (spectral) karyotypes and to detect chromosomal aberrations.

First, provided is a method for preparing a reference template for chromosome classification which includes (a) obtaining at least one sample of a complete set of metaphase chromosomes of a species having L types of chromosomes, the chromosomes of each of the at least one sample being preclassified via a conventional chromosome classification technique; (b) painting the chromosomes of each of the at least one samples with L different fluorophores-or-combinations-of-fluorophores, such that chromosomes which belong to each of the L types are differently painted; (c) using a spectral imager to measure a spectral cube for each of the at least one samples, such that at least one spectral cube is obtained; (d) employing a decorrelation statistical method, such as but not limited to principal component analysis, canonical variable analysis and singular value, etc., to extract decorrelated spectral data characterizing each of the L types of preclassified chromosomes; and (e) using at least a part of the decorrelated spectral data for the preparation of the reference template for chromosome classification.

In a preferred embodiment a principal component analysis is employed and includes the steps of (a) selecting k spectral slices for each spectral cube of each of the at least one samples; (b) calculating an average spectrum for each of the chromosomes; (c) stretching each of the average spectra for obtaining a stretched average spectrum for each of the chromosomes; (d) averaging the stretched average spectra for each of the L chromosome types for obtaining an ensemble average spectrum for each of the L types of chromosomes; (e) calculating an eigen system for the covariance matrix of the L ensemble average spectra and extracting N eigenvectors of this matrix; (f) using the N eigenvectors for defining an N-dimension vector for each of the L chromosome types; and (g) using the L N-dimension vectors for preparing the reference template for chromosome classification. Preferably the principal component analysis further includes (h) performing a spatial averaging procedure on all spectral slices; and (i) performing a background subtraction procedure.

Second, provided is a method for chromosome classification employing the reference template as described above, the method includes the steps of (a) obtaining a sample of chromosomes of a species having L types of chromosomes; (b) painting the chromosomes with L different fluorophores-or-combinations-of-fluorophores, such that chromosomes which belong to each of the L types are differently painted; (c) using a spectral imager to measure a spectral cube for the sample, such that a spectrum of each pixel in the sample is obtained; (d) employing a decorrelation statistical method to extract decorrelated spectral data characterizing each of the pixels; and (e) comparing at least a part of the decorrelated spectral data with the reference template. Preferably the method further includes the step of (f) according to the comparison, attributing each pixel an artificial color selected from L different types of colors.

Third, provided is a method for chromosome classification employing the reference template as described above, the method includes the steps of (a) obtaining a sample of chromosomes of a species having L types of chromosomes; (b) painting the chromosomes with L different fluorophores-or-combinations-of-fluorophores, such that chromosomes which belong to each of the L types are differently painted; (c) using a spectral imager to measure a spectral cube for the sample, such that a spectrum of each pixel in the sample is obtained; (d) projecting the spectrum of each of the pixels into the N decorrelated eigenvectors for obtaining a projected N dimension vector for each of the pixels; and (e) correlating each of the N dimension vectors with the reference template. Preferably the method further includes the steps of (h) performing a spatial averaging procedure on all spectral slices; and (i) performing a background subtraction procedure.

Fourth, provided is a method of calculating decorrelation matched filters for chromosome classification employing the reference template (N eigenvectors) as described above, the decorrelation matched filters are used for extracting decorrelated spectral data from chromosome samples painted according to a specific experimental protocol, the method includes the step of mathematically manipulating the at least part of the decorrelated spectral data for obtaining a mathematical description of the decorrelation matched filters.

Fifth, provided is a method for chromosome classification employing the reference template as described above, the method includes the steps of (a) obtaining a sample of chromosomes of a species having L types of chromosomes; (b) painting the chromosomes with L different fluorophores-or-combinations-of-fluorophores, such that chromosomes which belong to each of the L types are differently painted; (c) calculating a mathematical description of decorrelation matched filters for chromosome classification employing the reference template, the calculation being by mathematically manipulating the at least part of the decorrelated spectral data; (d) using the mathematical description of the decorrelation matched filters for manufacturing the decorrelation matched filters; (e) using the decorrelation matched filters for extracting decorrelated spectral data from each pixel of the chromosomes sample; and (f) comparing the decorrelated spectral data with the reference template. Preferably the method further includes the step of (g) attributing each pixel an artificial color selected from L different types of colors, according to the comparison.

Sixth, provided is a set of decorrelation matched filters for chromosome classification, the decorrelation matched filters being for extracting decorrelated spectral data from chromosome samples painted according to a specific experimental protocol, the set of decorrelation matched filters is manufactured according to the mathematical description as described above.

Seventh, provided is a set of information for implementing decorrelation matched filters for chromosome classification via a tunable filter, the implemented decorrelation matched filters being for extracting decorrelated spectral data from chromosome samples painted according to a specific experimental protocol, the set of information is calculated according to the mathematical description as described above. Preferably the tunable filter is AOTF or LCTF.

Eighth, provided is a method for chromosome classification employing the decorrelation matched filters for chromosome classification as described above, the method includes the steps of (a) obtaining a sample of chromosomes of a species having L types of chromosomes; (b) painting the chromosomes with L different fluorophores-or-combinations-of-fluorophores, such that chromosomes which belong to each of the L types are differently painted; (c) using the decorrelation matched filters for extracting decorrelated spectral data from each pixel of the chromosomes sample; and (d) comparing the decorrelated spectral data with the reference template. Preferably the method further includes the step of (e) according to the comparison, attributing each pixel an artificial color selected from L different types of colors.

Ninth, provided is a method for chromosome classification employing the information for implementing decorrelation matched filters for chromosome classification as described above, the method comprising the steps of (a) obtaining a sample of chromosomes of a species having L types of chromosomes; (b) painting the chromosomes with L different fluorophores-or-combinations-of-fluorophores, such that chromosomes which belong to each of the L types are differently painted; (c) using the information for implementing decorrelation matched filters by the tunable filter for extracting decorrelated spectral data from each pixel of the chromosomes sample; and (d) comparing the decorrelated spectral data with the reference template.

Tenth, provided is a spectral decorrelation measurement apparatus for chromosome classification by extracting decorrelated spectral data from a chromosome sample painted according to a specific experimental protocol, the apparatus is connected to a microscope used to view the sample, the apparatus includes (a) a light source; (b) a detector; and (c) an optical system for transmitting excitation light from the light source onto the sample and emission light from the sample onto the detector, the optical system including a set of decorrelating matched filters, the decorrelation matched filters being for extracting decorrelated spectral data from the chromosome sample painted according to the specific experimental protocol, the set of decorrelation matched filters being manufactured according to the mathematical description of as described above. Preferably the optical system further includes (i) an excitation filter placed in the path of light emitted from the light source for transmitting light in the range required for excitation of fluorophores contained in the sample and for blocking light in the range of emission; (ii) a dichroic filter for directing exiting light from the filter to the sample and emission light from the sample to the detector; and (iii) a focusing lens for focusing emitted light onto the detector. More preferably the optical system further includes a barrier filter for blocking any residual photons which are not in the spectral range of emission and a collimating lens for collimating light reaching to any of the decorrelating matched filters. Yet more preferably the decorrelation matched filters are arranged on a rotatable filter carrying element.

Eleventh, provided is a spectral decorrelation measurement apparatus for chromosome classification by extracting decorrelated spectral data from a chromosome sample painted according to a specific experimental protocol, the apparatus is connected to a microscope used to view the sample, the apparatus comprising (a) a light source; (b) a detector; and (c) an optical system for transmitting excitation light from the light source onto the sample and emission light from the sample onto the detector, the optical system including a tunable filter and a tuning device, the tuning device being for tuning the tunable filter to sequentially implement a set of decorrelating matched filters, the sequentially implemented decorrelation matched filters being for extracting decorrelated spectral data from the chromosome sample painted according to the specific experimental protocol, the tuning of the tunable filter being calculated according to the mathematical description of claim as described above.

The following embodiments of the invention concern a method and hardware for obtaining a multicolor banding pattern of chromosomes (i.e., bar-coding, multicolor banding karyotype).

Twelfth, provided is a method for preparing a reference template for chromosome banding analysis, the method comprising the steps of (a) obtaining at least one sample of a complete set of metaphase chromosomes of a species having L types of chromosomes, the chromosomes of each of the at least one sample being preclassified via a conventional chromosome classification technique; (b) painting the chromosomes of each of the at least one samples with different fluorophores-or-combinations-of-fluorophores, such that fragments of each of the L chromosome types are differently painted; (c) using a spectral imager to measure a spectral cube for each of the at least one samples, such that at least one spectral cube is obtained; (d) employing a decorrelation statistical method to extract decorrelated spectral data characterizing each of the fragments of preclassified chromosomes; and (e) using at least a part of the decorrelated spectral data for the preparation of the reference template for chromosome banding analysis. Preferably, the decorrelation statistical method is principal component analysis, canonical variable analysis or singular value decomposition, etc. In a preferred embodiment, the principal component analysis includes expressing each of the fragments as linear combinations of N eigenvectors. In another preferred embodiment, the principal component analysis includes the steps of (a) selecting k spectral slices for each spectral cube of each of the at least one samples; (b) calculating an average spectrum for each of the fragments; (c) stretching each of the average spectra for obtaining a stretched average spectrum for each of the fragments; (d) averaging the stretched average spectra for each of the fragments for obtaining an ensemble average spectrum for each of the fragments; (e) calculating a k dimension eigen system for the ensemble average spectra and extracting N eigenvectors; (f) using the N eigenvectors for defining an N-dimension vector for each of fragments; and (g) using the N-dimension vectors for preparing the reference template for chromosome banding analysis. In still another preferred embodiment, the principal component analysis further includes (h) performing a spatial averaging procedure on all spectral slices; and (i) performing a background subtraction procedure.

Thirteenth, provided is a method for chromosome banding analysis employing the reference template for chromosome banding as described above, the method comprising the steps of (a) obtaining a sample of chromosomes of a species having L types of chromosomes; (b) painting the chromosomes with different fluorophores-or-combinations-of-fluorophores, such that fragments of each of the L chromosome types are differently painted; (c) using a spectral imager to measure a spectral cube for the sample, such that a spectrum of each pixel in the sample is obtained; (d) employing a decorrelation statistical method to extract decorrelated spectral data characterizing each of the pixels; and (e) comparing at least a part of the decorrelated spectral data with the reference template.

Fourteenth, provided is a method for chromosome banding analysis employing the reference template for chromosome banding as described above, the method comprising the steps of (a) obtaining a sample of chromosomes of a species having L types of chromosomes; (b) painting the chromosomes with different fluorophores-or-combinations-of-fluorophores, such that fragments of each of the L chromosome types are differently painted; (c) using a spectral imager to measure a spectral cube for the sample, such that a spectrum of each pixel in the sample is obtained; (d) projecting the spectrum of each of the pixels onto the decorrelated spectral data for obtaining a projected spectrum for each of the pixels; and (e) comparing the projected spectra with the reference template. Preferably the method further comprising the step of (f) according to the comparison, attributing each pixel an artificial color.

Fifteenth, provided is a method for chromosome banding analysis employing the reference template for chromosome banding as described above, the method comprising the steps of (a) obtaining a sample of chromosomes of a species having L types of chromosomes; (b) painting the chromosomes with different fluorophores-or-combinations-of-fluorophores, such that fragments of each of the L chromosome types are differently painted; (c) using a spectral imager to measure a spectral cube for the sample, such that a spectrum of each pixel in the sample is obtained; (d) projecting the spectrum of each of the pixels into the N eigenvectors for obtaining a projected N dimension vector for each of the pixels; and (e) correlating each of the projected N dimension vectors with the reference template. Preferably, the method further comprising the steps of (h) performing a spatial averaging procedure on all spectral slices; and (i) performing a background subtraction procedure.

Sixteenth, provided is a method of calculating decorrelation matched filters for chromosome banding analysis employing the reference template for chromosome banding as described above, the decorrelation matched filters being for extracting decorrelated spectral data from chromosome samples painted according to a specific chromosome banding experimental protocol, the method comprising the step of mathematically manipulating the at least part of the decorrelated spectral data for obtaining a mathematical description of the decorrelation matched filters. Preferably, the decorrelated spectral data is obtained using a principal component analysis which includes expressing each of the chromosome fragments by a linear combination of N eigenvectors.

Seventeenth, provided is a set of decorrelation matched filters for chromosome banding analysis, the decorrelation matched filters being for extracting decorrelated spectral data from chromosome samples painted according to a specific experimental banding protocol, the set of decorrelation matched filters is manufactured according to the mathematical description described above.

Eighteenth, provided is a set of information for implementing decorrelation matched filters for chromosome banding analysis via a tunable filter, the decorrelation matched filters being for extracting decorrelated spectral data from chromosome samples painted according to a specific experimental banding protocol, the set of information is calculated according to the mathematical description as described above. Preferably the tunable filter is selected from the group consisting of AOTF and LCTF.

Nineteenth, provided is a method for chromosome banding analysis employing the reference template for chromosome banding as described above, the method comprising the steps of (a) obtaining a sample of chromosomes of a species having L types of chromosomes; (b) painting the chromosomes with different fluorophores-or-combinations-of-fluorophores, such that fragments of each of the L chromosome types are differently painted; (c) calculating a mathematical description of decorrelation matched filters for chromosome banding analysis employing the reference template, the calculation being by mathematically manipulating the at least part of the decorrelated spectral data; (d) using the mathematical description of the decorrelation matched filters for manufacturing the decorrelation matched filters; (e) using the decorrelation matched filters for extracting decorrelated spectral data from each pixel of the chromosomes sample; and (f) comparing the decorrelated spectral data with the reference template. Preferably, the method further comprising the step of (g) attributing each pixel an artificial color according to the comparison.

Twentieth, provided is a method for chromosome banding analysis employing the decorrelation matched filters for chromosome banding analysis as described above, the method comprising the steps of (a) obtaining a sample of chromosomes of a species having L types of chromosomes; (b) painting the chromosomes with different fluorophores-or-combinations-of-fluorophores, such that fragments of each of the L chromosome types are differently painted; (c) using the decorrelation matched filters for extracting decorrelated spectral data from each pixel of the chromosomes sample; and (d) comparing the decorrelated spectral data with the reference template.

Twenty first, provided is a method for chromosome banding analysis employing the information for implementing decorrelation matched filters for chromosome banding analysis as described above, the method comprising the steps of (a) obtaining a sample of chromosomes of a species having L types of chromosomes; (b) painting the chromosomes with different fluorophores-or-combinations-of-fluorophores, such that fragments of each of the L chromosome types are differently painted; (c) using the information for implementing decorrelation matched filters by the tunable filter for extracting decorrelated spectral data from each pixel of the chromosomes sample; and (d) comparing the decorrelated spectral data with the reference template.

Preferably, the method further comprising the step of (e) according to the comparison, attributing each pixel an artificial color.

Twenty second, provided is a spectral decorrelation measurement apparatus for chromosome banding analysis by extracting decorrelated spectral data from a chromosome sample painted according to a specific experimental banding protocol, the apparatus is connected to a microscope used to view the sample, the apparatus comprising (a) a light source; (b) a detector; and (c) an optical system for transmitting excitation light from the light source onto the sample and emission light from the sample onto the detector, the optical system including a set of decorrelating matched filters, the decorrelation matched filters being for extracting decorrelated spectral data from the chromosome sample painted according to the specific experimental banding protocol, the set of decorrelation matched filters being manufactured according to the mathematical description described above.

Twenty third, provided is a spectral decorrelation measurement apparatus for chromosome banding analysis by extracting decorrelated spectral data from a chromosome sample painted according to a specific experimental banding protocol, the apparatus is connected to a microscope used to view the sample, the apparatus comprising (a) a light source; (b) a detector; and (c) an optical system for transmitting excitation light from the light source onto the sample and emission light from the sample onto the detector, the optical system including a tunable filter and a tuning device, the tuning device being for tuning the tunable filter to sequentially implement a set of decorrelating matched filters, the sequentially implemented decorrelation matched filters being for extracting decorrelated spectral data from the chromosome sample painted according to the specific experimental protocol, the tuning of the tunable filter being calculated according to the mathematical description as described above.

Preferably the optical system further includes (i) an excitation filter placed in the path of light emitted from the light source for transmitting light in the range required for excitation of fluorophores contained in the sample and for blocking light in the range of emission; (ii) a dichroic filter for directing exiting light from the filter to the sample and emission light from the sample to the detector; and (iii) a focusing lens for focusing emitted light onto the detector. More preferably the optical system further includes a barrier filter for blocking any residual photons which are not in the spectral range of emission and a collimating lens for collimating light reaching to any of the decorrelating matched filters. Yet more preferably the decorrelation matched filters are arranged on a rotatable filter carrying element.

And finally, according to preferred embodiments for both chromosome classification and chromosome banding analysis (i) the species is human and L equals 24; (ii) the painting is by combinatorial fluorescent strategy of combinatorial labeling or combinatorial hybridization; (iii) the decorrelation statistical method is principal component analysis, canonical variable analysis or singular value decomposition, etc.; (iv) the principal component analysis includes expressing each of the L types of chromosomes as linear combinations of N eigenvectors, preferably N is an integer greater than two, more preferably N is an integer greater than two and smaller than eight; (v) k is an integer greater than nine, k is preferably selected between nine and twenty one, yet larger values for k are also possible; (vi) the chromosomes are metaphase chromosomes, interphase chromosomes or chromosomes undergoing meiosis; (vii) the chromosomes are of a fetal cell, a cancerous cell or an adult healthy cell; and (viii) the chromosomes are of a solid tumor cell or a blood tumor cell.

Reference is now made to the following examples, which together with the above descriptions, illustrate the invention.

EXAMPLE 1

Chromosome Preparation for Measurement

The emergence of multicolor FISH has broadened the applications of molecular cytogenetics in basic research and genetic diagnosis. All existing multicolor FISH techniques require the use of fluorescent probes whose emission spectra can be separated with optical filters [Ried et al., (1992) Simultaneous visualization of seven different DNA probes by in situ hybridization using combinatorial fluorescence and digital imaging microscopy. Proc. Natl. Acad. Sci. USA 89, 1388–1392; and, Ried (January 1994) Fluoreszenz in situ Hybridizierung in der genetischen Diagnostik, Faculty of theoretical medicine, Ruprecht-Karls University Heidelberg, both are incorporated by reference as if fully set forth herein]. This requirement limits the number of dyes which can be distinguished in a given sample.

A novel approach for FISH, employing the SpectraCube™ system to measure and analyze multiple spectrally overlapping labeled probes (single and combinatorial), to classify chromosomes and therefore to detect chromosomal aberrations was recently introduced [E. Schroeck et al. (1996) Multicolor spectral karyotyping of human chromosomes. Science, 273, 494–497].

According to that novel approach, spectral bio-imaging which is a combination of Fourier spectroscopy, CCD-imaging and optical microscopy enabling the measurement of accurate spectral data simultaneously at all points of a biological sample, was used to visualize hybridization based multicolor appearance of all (i.e., 24) types of human chromosomes and to generate a color map of the human karyotype.

According to the present invention, data spectrally collected by any spectral imager having a spectral resolution of 20 nm or higher (i.e., $\Delta\lambda < 20$ nm) is statistically analyzed using decorrelation statistical methods such as but not limited to principal component analysis (PCA) to find correlations among the data and to construct (i) a reference template which may then be used for routine analysis of new samples; and (ii) a hardware based on decorrelation matched filters (fixed or tunable) for collecting only the decorrelated spectral data (a smaller amount than with prior art), from new samples while the correlated data are averaged over at the outset, thereby decreasing measurement time and increasing signal to noise ratio. Both the reference template and the decorrelation matched filters (or their tuned implementation effected by a tunable filter) according to the invention can be used to classify chromosomes and to detect chromosomal aberrations.

As will be described in more detail below, both the reference template and the decorrelation matched filters (or their tuned implementation using a tunable filter) according to the invention are dedicated to a given experimental procedure in which the dyes and their combinations which are used to label any of the chromosomes are predetermined. It will be appreciated by one ordinarily skilled in the art that many different sets of fluorophores and combinations thereof can be used to specifically label each of the 24 chromosomes of human or each chromosome of any other species. In this example a set of five dyes from which combinations of up to three dyes are used to differently label each of the 24 human chromosomes is used. However, the use of these dyes or combinations is for illustrative purpose only, and there is no intention to limit the scope of the invention to use of any specific dyes and/or combinations thereof. Following is a description of the dyes and their combinations which are presently preferred, to which dyes and combinations the construction of a reference template and decorrelation matched filters as described in the Examples to follow are dedicated.

Thus, 24 chromosome paints (1 through 22, X and Y, Table 1), each labeled with a different combination of three or less different flourophores selected from a set of five fluorophores according to the combinatorial hybridization approach (a through e, Table 1), (see Table 1 for the different fluorophores and their spectral characteristics and Table 2 for the assignment of the fluorophores listed in Table 1 to obtain the 24 chromosome paints), were simultaneously hybridized with human mitotic chromosome spreads of few non-related male white blood cells, prepared for hybridization essentially as described in Ried et al. [Ried et al., (1992) Simultaneous visualization of seven different DNA probes by in situ hybridization using combinatorial fluorescence and digital imaging microscopy. Proc. Natl. Acad. Sci. USA 89, 1388–1392].

Hybridized chromosomes were viewed through an inverted fluorescence microscope connected to the SpectraCube™ System and were analyzed.

It is clear to one ordinarily skilled in the art that other fluorophores, other combinations of fluorophores and different labeling approaches (e.g., combinatorial labeling) can be similarly used. Thus the body of information listed hereinbelow in Tables 1 and 2 is of an illustrative nature only, and there is no intention to limit the scope of the invention to the listed fluorophores, combinations of fluorophores and/or labeling technique.

TABLE 1

| Fluorophore | Symbol | Excitation (nm) |
|---|---|---|
| FITC or Spectrum Green | a | 475–495 |
| Cy5 ™[1] | b | 630–670 |
| Cy3 ™[1] | c | 540–570 |
| Texas-Red | d | 540–570 |
| Cy5.5 ™[1] | e | 630–670 |

[1]from Amersham

TABLE 2

| Chromosome | Chromosome paint | Fluorophores |
|---|---|---|
| human chromosome 1 | 1 | b, c, d |
| human chromosome 2 | 2 | e |
| human chromosome 3 | 3 | a, c, e |
| human chromosome 4 | 4 | c, d |
| human chromosome 5 | 5 | a, b, e |
| human chromosome 6 | 6 | b, d, e |
| human chromosome 7 | 7 | b, c |
| human chromosome 8 | 8 | a, b, c |
| human chromosome 9 | 9 | a, d, e |
| human chromosome 10 | 10 | c, e |
| human chromosome 11 | 11 | a, c, d |
| human chromosome 12 | 12 | b, e |
| human chromosome 13 | 13 | a, d |
| human chromosome 14 | 14 | b |
| human chromosome 15 | 15 | a, e |
| human chromosome 16 | 16 | b, d |
| human chromosome 17 | 17 | a, c |
| human chromosome 18 | 18 | a, b, d |
| human chromosome 19 | 19 | c |
| human chromosome 20 | 20 | a |
| human chromosome 21 | 21 | d, e |
| human chromosome 22 | 22 | b, c, e |
| human chromosome X | X | c, d, e |
| human chromosome Y | Y | d |

EXAMPLE 2

The Measurement Apparatus

FIG. 1 is a block diagram illustrating the main components of a prior art imaging spectrometer disclosed in U.S. Pat. No. 5,539,517 to Cabib et al., filed Feb. 21st, 1995 which is incorporated by reference as if fully set forth herein. This imaging spectrometer is constructed highly suitable to implement the method of the present invention as it has high spectral (Ca. 4–14 nm depending on wavelength) and spatial (Ca. 30/M $\mu$m where M is the effective microscope or fore optics magnification) resolutions.

Thus, the prior art imaging spectrometer of FIG. 1 includes: a collection optical system, generally designated 20; a one-dimensional scanner, as indicated by block 22; an optical path difference (OPD) generator or interferometer, as indicated by block 24; a one-dimensional or two-dimensional detector array, as indicated by block 26; and a signal processor and display, as indicated by block 28.

A critical element in system 20 is the OPD generator or interferometer 24, which outputs modulated light corresponding to a predetermined set of linear combinations of the spectral intensity of the light emitted from each pixel of the scene to be analyzed. The output of the interferometer is focused onto the detector array 26. Thus, all the required optical phase differences are scanned simultaneously for all the pixels of the field of view, in order to obtain all the information required to reconstruct the spectrum. The spectra of all the pixels in the scene are thus collected simultaneously with the imaging information, thereby permitting analysis of the image in a real-time manner.

The apparatus according to U.S. Pat. No. 5,539,517 may be practiced in a large variety of configurations. Specifically, the interferometer used may be combined with other mirrors as described in the relevant Figures of U.S. Pat. No. 5,539,517.

Thus, according to U.S. Pat. No. 5,539,517, alternative types of interferometers may be employed. These include (1) a moving type interferometer in which the OPD is varied to modulate the light, namely, a Fabry-Perot interferometer with scanned thickness; (2) a Michelson type interferometer which includes a beamsplitter receiving the beam from an optical collection system and a scanner, and splitting the beam into two paths; (3) a Sagnac interferometer optionally combined with other optical means in which interferometer the OPD varies with the angle of incidence of the incoming radiation, such as the four-mirror plus beamsplitter interferometer as further described in the cited U.S. Pat. application (see FIG. 14 there).

Figure 2:
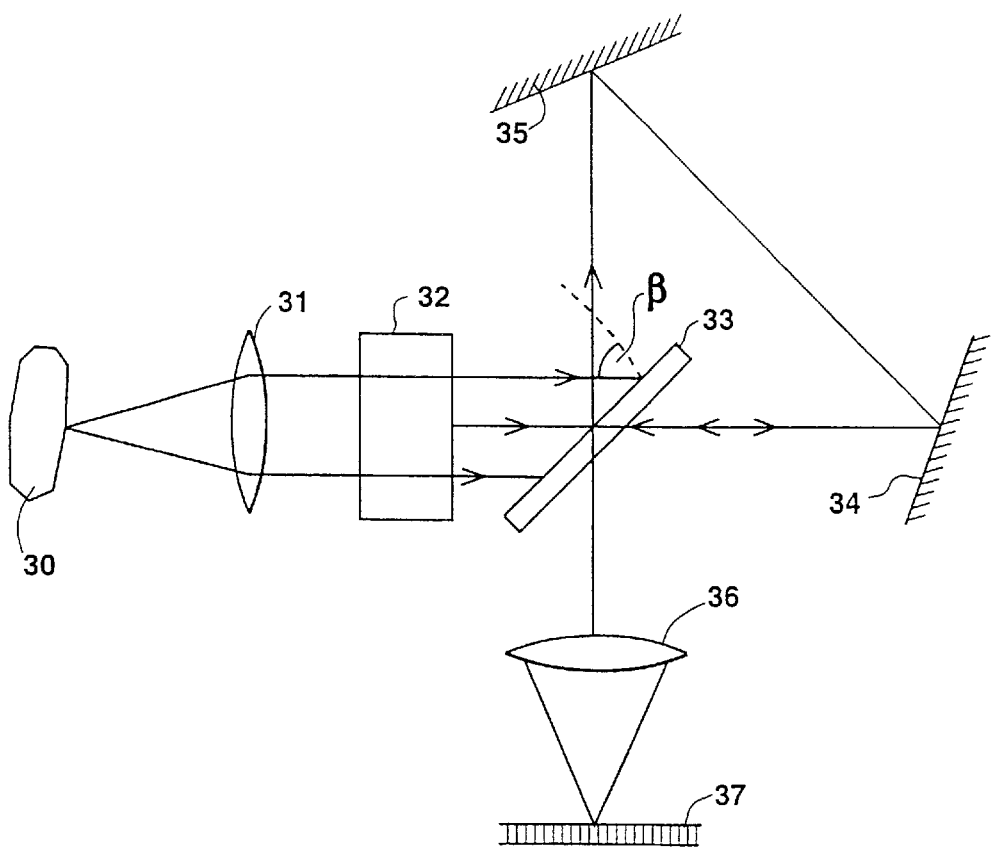
FIG. 2 illustrates a Sagnac interferometer, as used in an imaging spectrometer in accordance with U.S. Pat. No. 5,539,517 (prior art)

FIG. 2 illustrates an imaging spectrometer constructed in accordance with U.S. Pat. No. 5,539,517 utilizing an interferometer in which the OPD varies with the angle of incidence of the incoming radiation. A beam entering the interferometer at a small angle to the optical axis undergoes an OPD which varies substantially linearly with this angle.

In the interferometer of FIG. 2, all the radiation from source 30 in all the pixels, after being collimated by an optical collection system 31, is scanned by a mechanical scanner 32. The light is then passed through a beamsplitter 33 to a first reflector 34 and then to a second reflector 35, which reflects the light back through the beamsplitter 33 and then through a focusing lens 36 to an array of detectors 37 (e.g., a CCD). This beam interferes with the beam which is reflected by 33, then by second reflector 35, and finally by first reflector 34.

At the end of one scan, every pixel has been measured through all the OPD's, and therefore the spectrum of each pixel of the scene can be reconstructed by Fourier transformation. A beam parallel to the optical axis is compensated, and a beam at an angle ($\theta$) to the optical axis undergoes an OPD which is a function of the thickness of the beamsplitter 33, its index of refraction, and the angle $\theta$. The OPD is proportional to $\theta$ for small angles. By applying the appropriate inversion, and by careful bookkeeping, the spectrum of every pixel is calculated.

In the configuration of FIG. 2 the ray which is incident on the beamsplitter at an angle $\beta$ ($\beta=45°$ in FIG. 2) goes through the interferometer with an OPD=0, whereas a ray which is incident at a general angle $\beta-\theta$ undergoes an OPD given by Equation 2:

$$OPD(\beta,\theta,t,n)=t[(n^2-\sin^2(\beta+\theta))^{0.5}-(n^2-\sin^2(\beta-\theta))^{0.5}+2\sin\beta\sin\theta]$$

where $\beta$ is the angle of incidence of the ray on the beamsplitter; $\theta$ is the angular distance of a ray from the optical axis or interferometer rotation angle with respect to the central position; t is the thickness of the beamsplitter; and n is the index of refraction of the beamsplitter.

It follows from Equation 2 that by scanning both positive and negative angles with respect to the central position, one can get a double-sided interferogram for every pixel, which helps eliminate phase errors giving more accurate results in the Fourier transform calculation. The scanning amplitude determines the maximum OPD reached, which is related to the spectral resolution of the measurement. The size of the angular steps determines the OPD step which is, in turn, dictated by the shortest wavelength to which the system is sensitive. In fact, according to the sampling theorem [see, Chamberlain (1979) The principles of interferometric spectroscopy, John Wiley and Sons, pp. 53–55], this OPD step must be smaller than half the shortest wavelength to which the system is sensitive.

Another parameter which should be taken into account is the finite size of a detector element in the matrix. Through the focusing optics, the element subtends a finite OPD in the interferometer which has the effect of convolving the interferogram with a rectangular function. This brings about, as a consequence, a reduction of system sensitivity at short wavelengths, which drops to zero for wavelengths equal to or below the OPD subtended by the element. For this reason, one must ensure that the modulation transfer function (MTF) condition is satisfied, i.e., that the OPD subtended by a detector element in the interferometer must be smaller than the shortest wavelength at which the instrument is sensitive.

Thus, imaging spectrometers constructed in accordance with the invention disclosed in U.S. Pat. No. 5,539,517 do not merely measure the intensity of light coming from every pixel in the field of view, but also measure the spectrum of each pixel in a predefined wavelength range. They also better utilize all the radiation emitted by each pixel in the field of view at any given time, and therefore permit, as explained above, a significant decrease in the frame time and/or a significant increase in the sensitivity of the spectrometer. Such imaging spectrometers may include various types of interferometers and optical collection and focusing systems, and may therefore be used in a wide variety of applications, including medical diagnostic and therapy and biological research applications, as well as remote sensing for geological and agricultural investigations, and the like.

As mentioned above, an imaging spectrometer in accordance with the invention disclosed in U.S. Pat. No. 5,539,517 was developed by Applied Spectral Imaging Ltd., Industrial Park, Migdal Haemek, Israel and is referred herein as SpectraCube™.

The SpectraCube™ system optically connected to a variety of optical devices is used to implement the method of the present invention. The SpectraCube™ system has the following characteristics, listed hereinbelow in Table 3:

TABLE 3

| Character | Performance |
| --- | --- |
| Spatial resolution: | 30/M μm (M = effective microscope or fore optics magnification) |
| Field of View: | 8/M millimeter |
| Sensitivity: | 20 milliLux (for 100 msec integration time, increases for longer integration times linearly with √T) |
| Spectral range: | 400–1000 nm |
| Spectral resolution: | 4 nm at 400 nm (16 nm at 800 nm) |
| Acquisition time: | 5–50 sec, typical 25 sec |
| FFT processing time: | 20–180 sec, typical 60 sec |

The prior art SpectraCube™ system is used herein to acquire spectral data of every pixel of metaphase in situ painted chromosomes as described above. However, as specified above, any spectral imager, i.e., an instrument that measures and stores in memory for later retrieval and analysis the spectrum of light emitted by every point of an object which is placed in its field of view, including filter (e.g., acousto-optic tunable filters (AOTF) or liquid-crystal tunable filter (LCTF)) and dispersive element (e.g., grating) based spectral imagers can be used to acquire the required spectral data. Therefore, it is intended not to limit the scope of the present invention for use of any specific type of spectral imager.

EXAMPLE 3

Decorrelation Statistical Analysis for Chromosome Classification and for Designing Decorrelation Matched Filters Decorrelation statistical analysis is directed at extracting decorrelated data out of a greater amount of data, and average over the correlated portions thereof. There are a number of related statistical decorrelation methods. Examples include but not limited to principal component analysis (PCA), canonical variable analysis and singular value decomposition, etc., of these methods PCA is perhaps the more common one, and is used according to the present invention for decorrelation of spectral data, as this term is defined above. However, considering the fact that all decorrelation statistical methods including those listed above are related to one another, there is no intention to limit the scope of the invention to use of any specific decorrelation method. Specifically, there is no intention to limit the scope of the present invention to use of principal component analysis, as any other decorrelation statistical method may be alternatively employed. Information concerning the use and operation of the above listed decorrelation statistical methods is found in R. A. Johnson and D. W. Wichen, "Applied Multivariance Statistical Analysis", third edition, Prentice Hall (1992) and T. W. Anderson, An Introduction to Multivariance Statistical Analysis, second edition, Wiley and Sons (1984), both are incorporated by reference as if fully set forth herein.

Furthermore, as will become apparent from the descriptions to follow, the implementation of a decorrelation statistical method may be done using various modifications. As the concept of the present invention is not dependent upon any specific modification, it is the intention that the scope of the present invention will not be limited to any specific modification as described below.

Principal component analysis (PCA) is one of a number of powerful techniques used in multivariate statistical analysis. It is advantageous in cases where a large number of "results", which depend on a large number of possibly correlated variables forms the basic data set. Its strength lies in the fact that this data decomposition provides a transformation to decorrelated variables, while simultaneously averaging over correlated variables.

In this paragraph the PCA technique as applied to multi-spectral images of the same object is delineated. The basic data set, i.e., the spectral cube, is composed of k spectral slices of the same object, where each spectral slice is obtained at a different spectral band. Thus, the data set is composed of the spectra of all the pixels of the object. One of the objectives of looking at such a data set can be the characterization of the pixels into groups of similar spectra. Regard each spectral slice as a vector whose elements are the image pixels arranged into the column vector using a predetermined code. Call the spectral slices $X_m$, so that the term $x_{nm}$ signifies the n-th pixel of the m-th spectral slice. In such way, the matrix $x=\{x_{nm}\}$ carries the fall information, so that each column is a spectral slice. Define a matrix y derived from matrix x by subtracting from each column, the column average. The various columns of the y matrix may be correlated, so that, some of the information carried by the data is correlated. The PCA technique decorrelates the information and reduces it only to decorrelated variables, so that the amount of "real" data pixels is smaller and easier to handle.

The correlations are obtained directly by computing the covariance matrix c defined by Equation 3:

$$c = y'y \qquad (3)$$

where y' is the transpose of y. The i,j term of c is the covariance of the i-th slice with the j-th slice, i.e. if they are decorrelated this term vanishes. The diagonal of c is composed of the variances of each spectral slice, which can be regarded as a scale for the amount of information in this particular slice. Alternatively, this variance (its square root) can be regarded as the average contrast of this particular slice.

Linear algebra describes this situation as follows. The objects of interest (the pixels of the spectral slices, k of them) are points in a k dimensional space. The fact that the covariance matrix c shows correlations is represented by its having a rank smaller than k. This situation is called degeneracy and it means that the k (narrow band) spectral slices provide too much data relative to the information content. Reduction of the data is performed by finding the eigen system of the covariance matrix. Formally, this operation means that one has to find k vectors $v_m$ called eigenvectors and k scalars $\lambda_m$ called eigenvalues so that (Equation 4):

$$c.v_m = \lambda_m v_m \text{ for } m=1, 2, \ldots, k \qquad (4)$$

In a case where the data is correlated, some of the eigenvalues vanish. The number of non-vanishing eigenvalues defines the dimension of the information, which dimension is smaller than k. The corresponding eigenvectors define a subspace in the original k space in which the full information content is represented. Furthermore, the information in each new dimension is completely decorrelated to the information in the other dimensions. Thus in the new space the full information content is represented in a decorrelated manner so that it can be easily used for classification purposes. For further details regarding the principal component analysis, the reader is referred to Martens and Naes (1989) Multivariate Calibration, John Wiley & Sons, Great Britain; and to Esbensen et al., Eds. (1994) Multi variance analysis—in practice; and, Computer-aided modeling as CAMO, and the Unscrambler's User's guide, Trondheim, Norway, both are incorporated by reference as if fully set forth herein.

It should be noted that such an analysis can be performed on a whole spectral cube. Preferably, the analysis is performed only for selected pixels or mathematically manipulated (e.g., after background subtraction and averaging) selected pixels to improve the results and enable better classification later on. The preferred approach is described in more detail below, nevertheless, there is no intention to limit the scope of the present invention to the preferred approach employed, as different mathematical manipulations may be found useful for different data collection approaches (e.g., filter or dispersion element based spectral imagers) and/or different experimental conditions, e.g., fluorophores choice.

EXAMPLE 4

The Basic Data Set

The results of the spectral measurements of the stained chromosomes sample is stored in a spectral cube in any convenient format. In order to be able to access, for analysis purposes, each spectral cube a conversion is typically needed. The conversion can be performed by a dedicated software able to read each pixel in each spectral slice and write it into another file in a format suitable to the user. Alternatively, a commercial software, sold under the name ENVI (environment for visualizing images) by Research Systems Inc., Boulder Colo., USA, can be used. ENVI can read a spectral cube and write, on request, each spectral slice into a standard *.GIF format which can be read by a large number of routines. ENVI can be used in a different mode called the BSQ format. The later writes the cube in a binary sequential manner, starting at the spectral slice possessing the highest wave number, wherein each slice is written column after column.

Alternatively to the above approach, a dedicated software package can be written in an appropriate language, either stand alone or incorporated in the existing SpectraCube™ system software, to perform the building of the basic data set.

Both the GIF and the BSQ methods convert the data in an exact fashion, yet there is a difference that a user should be aware of. While converting by using the GIF transformation, each spectral slice is stretched to the full dynamic range thus loosing the relative intensities among the various spectral slices, but conserving the full information content in each, whereas according to the BSQ conversion, the entire spectral cube is converted, preserving the relative intensities in the entire cube. In a case where the user wishes to further perform a stretch the user can do it afterwards. This difference affects the PCA in a marginal way. Presently, the GIF approach is preferred.

For the present analysis twenty spectral slices derived from a spectral cube measured as described above were used. These were chosen out of a larger number of spectral slices of the cube. Those spectral slices utilized were those where significant contrast and low noise was present. It should be noted that any other number of spectral slices from about 10–15 or more (up to a limit which is determined by the spectral resolution of the spectral imager and the spectral range) can be used and that there is no intention to limit the scope of the invention to any specific number.

Figure 3A:
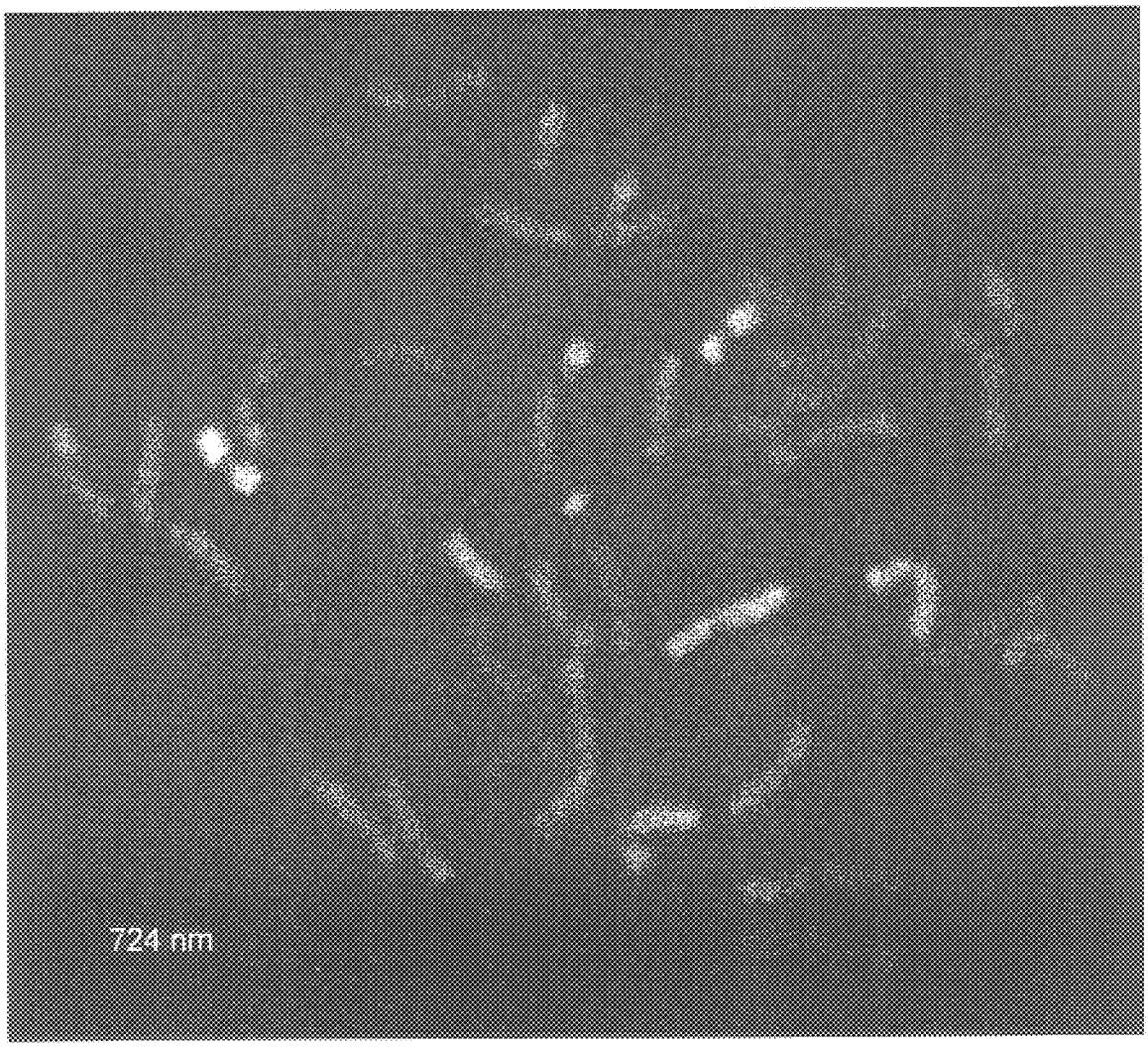
FIGS. 3a and 3b are chromosome images at spectral bands 724 nm and 597 nm, respectively, as derived from a spectral cube measured using the SpectraCube™ system.
Figure 3B:

FIGS. 3a–b, present two examples of the spectral slices, at 724 nm (FIG. 3a) and 597 nm (FIG. 3b). Notice the difference in contrast, noise and intensity over the various chromosomes.

EXAMPLE 5

Pre-Processing for Classification

For pre-processing, the k (e.g., twenty) spectral slices above are first used to find the decorrelated (and therefore orthogonal) principal components vectors of each chromosome type (L types in a species, 24 types in human), then the projection of each chromosome in each relevant principal component direction is calculated. This is equivalent to find the position of each chromosome template in the principal component space. This is performed by first identifying the chromosomes via conventional chromosome classification techniques, e.g., G-banding, R-banding or color karyotyping as described in E. Schroeck et al. (1996) Multicolor spectral karyotyping of human chromosomes, Science, 273, 494–497. It should be noted that the method described in science can be performed post G-banding or simultaneously to R-banding without affecting the measured spectral results.

As each of the chromosomes is labeled with a different fluorophore or a different combination of fluorophores, the projection of each chromosome onto each of the orthogonal principal components (PCs) forms a specifying reference vector (24 different vectors for a human male, 23 for a human female, different numbers for other species, generally L vectors for a species) which is unique to each of the chromosomes.

These L reference vectors collectively form a reference template for chromosome classification, as each of these L reference vectors is used as an identification means to attribute each pixel of a new spectral cube to one of the L chromosome types.

Therefore, these L different reference vectors, i.e., the reference template, can now be used to form an artificially colored karyotype of any spectral cube in which each of the chromosomes is attributed a different artificial color according to its type, selected from the L types of chromosomes in the studied species. This is done by a classification algorithm which compares measured vectors of pixels in a cube to be analyzed to the above reference vectors, followed by attributing each of the pixels a matching artificial color selected from L different artificial colors, according to the comparison results.

A preferred embodiment for pre-processing for classification is herein described in more detail:

For each staining technique at least one, preferably a number, of independently classified (e.g., G-banding) images are selected, from which a reference template is calculated as follows.

First, a 3×3 spatial averaging is performed on all selected k spectral slices such that each nine pixels are now attributed an average spectrum and are considered a single enlarged pixel. Although this procedure reduces the spatial resolution of the analysis, it is employed as it also reduces noise to a large extent. It should however be noted that this step was experimentally determined to be useful, yet as the amount of noise associated with other data collection approaches and/or experimental procedures may differ tremendously, there is no intention to limit the invention to a specific mode of averaging (e.g., 3×3) or to averaging altogether.

Second, an average spectrum of the whole cube(s), or the average spectrum of some, most or all the background pixels is calculated and is thereafter subtracted from the spectrum of each of the pixels in the cube. It will be appreciated that as most of the pixels in a cube are of background, the different calculated average spectra yield nearly identical results. Nevertheless, it should be noted that as the intensity of background may differ to a large extent while using other data collection approaches and/or experimental procedures, different background subtraction procedures may be employed. Furthermore, as in some cases background subtraction may be found improving results in a marginal way only, it may therefore, in these cases, be discarded altogether.

Third, each chromosome is masked, typically manually or with a suitable automatic image processing algorithm, and the average spectrum for each chromosome within its mask is calculated. As mentioned above under Example 3, the analysis can be performed on a whole spectral cube(s), yet preferably, the analysis is performed only for selected pixels or mathematically manipulated (e.g., after background subtraction and averaging) selected pixels to improve the results and enable better classification later-on.

Fourth, the average spectrum of each chromosome calculated above is separately stretched preferably into the maximal dynamic range 0–1.

Fifth, the stretched average spectra of the same chromosome types derived from different or same cube measurements is averaged to produce an ensemble average spectrum for each type of chromosome (collectively L types, 24 types for human). As is now apparent, presently it is preferred that the PCA will be performed on mathematically manipulated pixels. These are L (e.g., 24 for human) pixels each having a unique ensemble average spectrum which are mathematically manipulated as described. It should be noted however that one can obtain similar results also when applying the above described steps in a different order.

Sixth, an eigen system of the ensemble average spectra is calculated and the eigenvectors are used to calculate the PC of the ensemble average spectra.

To this end, the L chromosomes ensemble average spectra are stored in an L (e.g., 24 for human) line by k (e.g., 20) columns matrix, called matrix S, where each line represents a chromosome and each column a given spectral slice which are selected as described above under Example 3. The number k of spectral slices is not necessarily 20 and can be any number between substantially 10–15 or more, say 40, about equally spaced in the 500–800 nm region, depending on the emission spectra of the fluorophores employed, k is preferably selected to be an integer greater than nine.

C is defined as the covariance of S. C is typically a k×k (e.g., 20×20) matrix which represents the covariance between each pair of chromosomes. The eigen system of matrix C is calculated. V is defined as the matrix composed of the eigenvectors (each column being an eigenvector).

Figure 4:
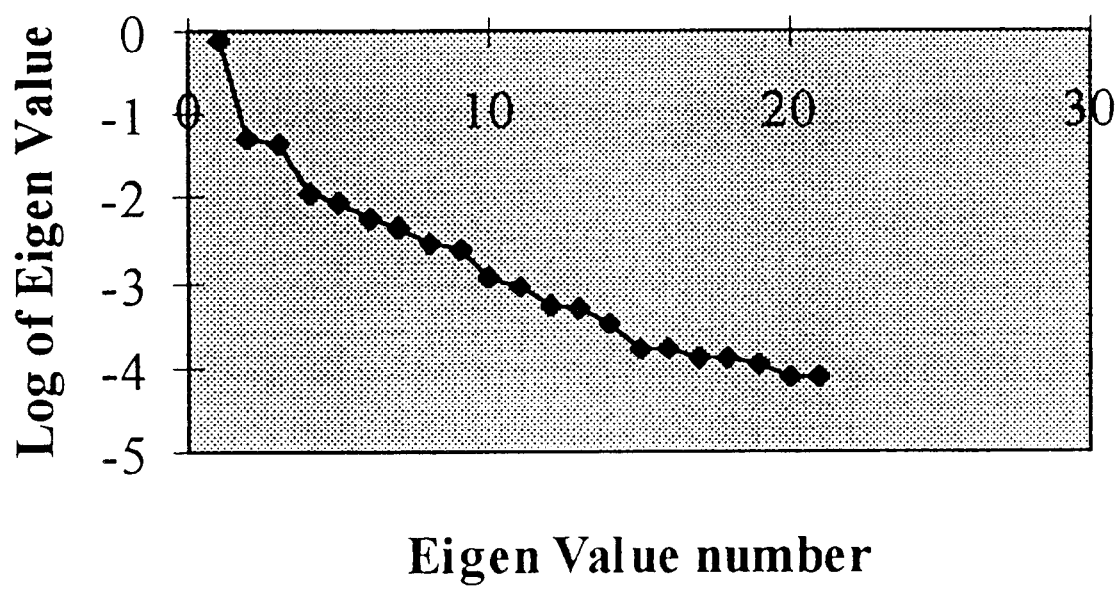
FIG. 4 is a graphic presentation of the twenty eigenvalues of the covariance matrix of the same spectral cube.
Figure 5A:
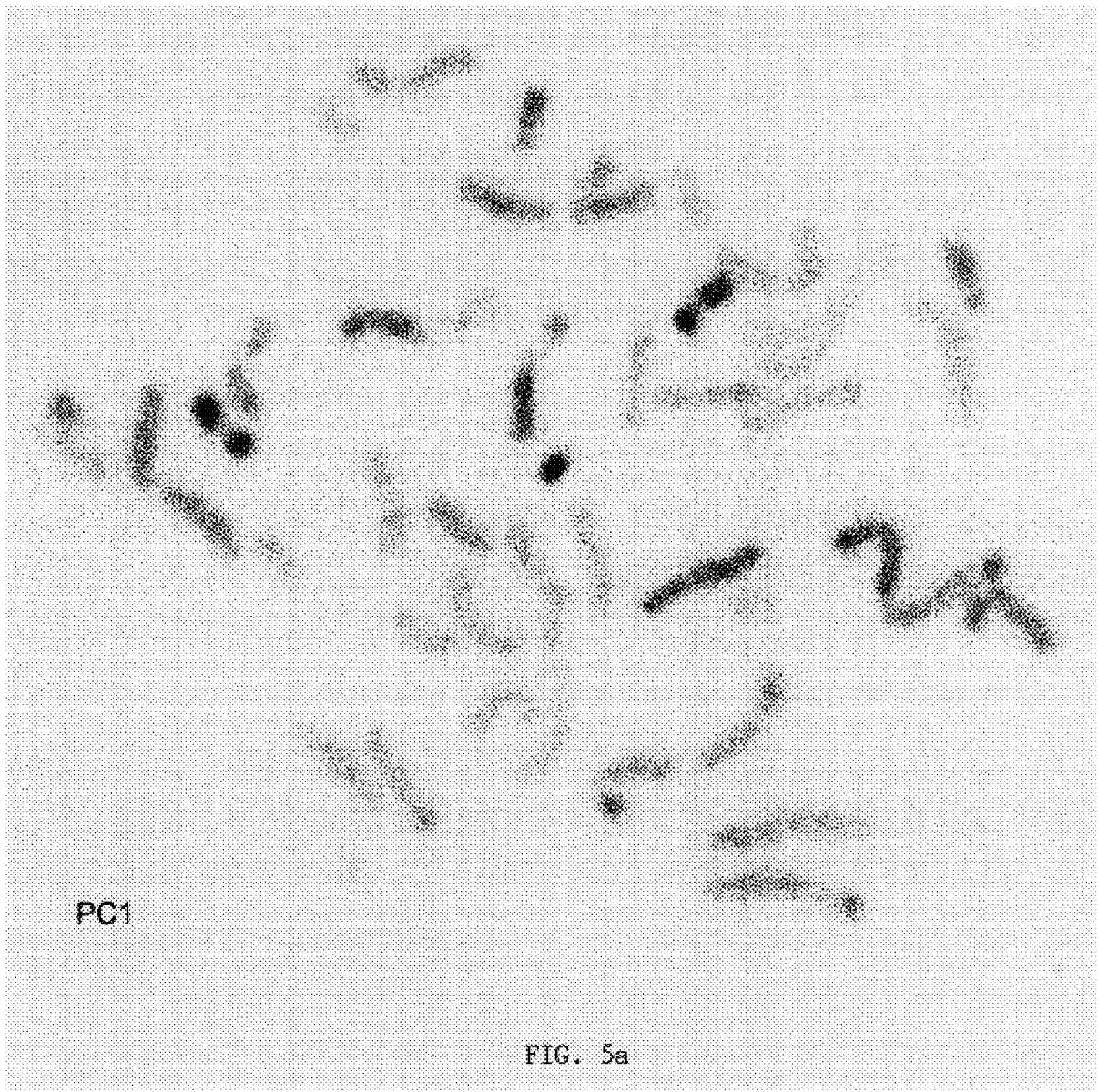
FIGS. 5a–e are the first five PCA images of the same spectral cube, shown after cube stretching to cover the full dynamic range of the display.
Figure 5B:
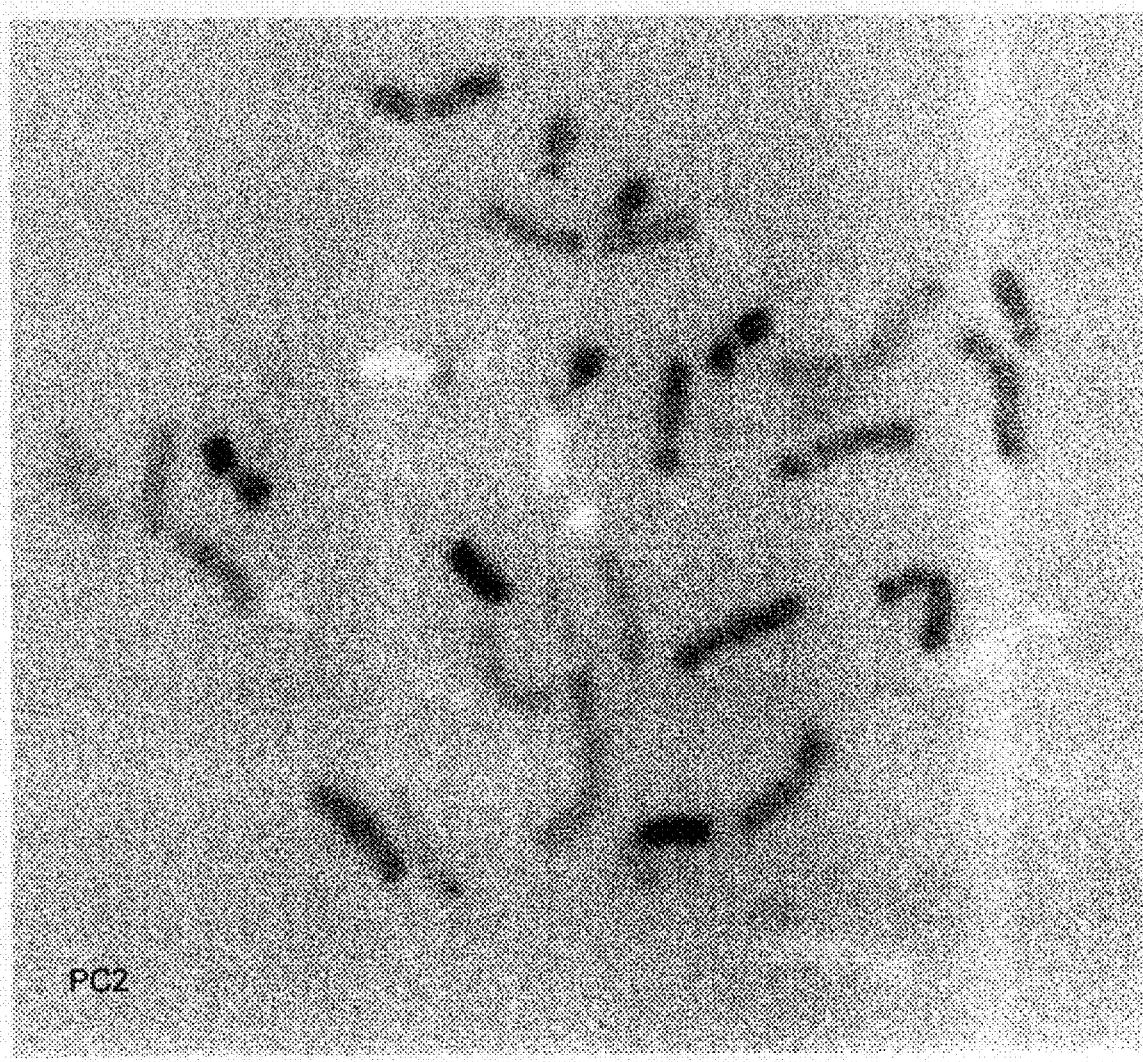
Figure 5C:
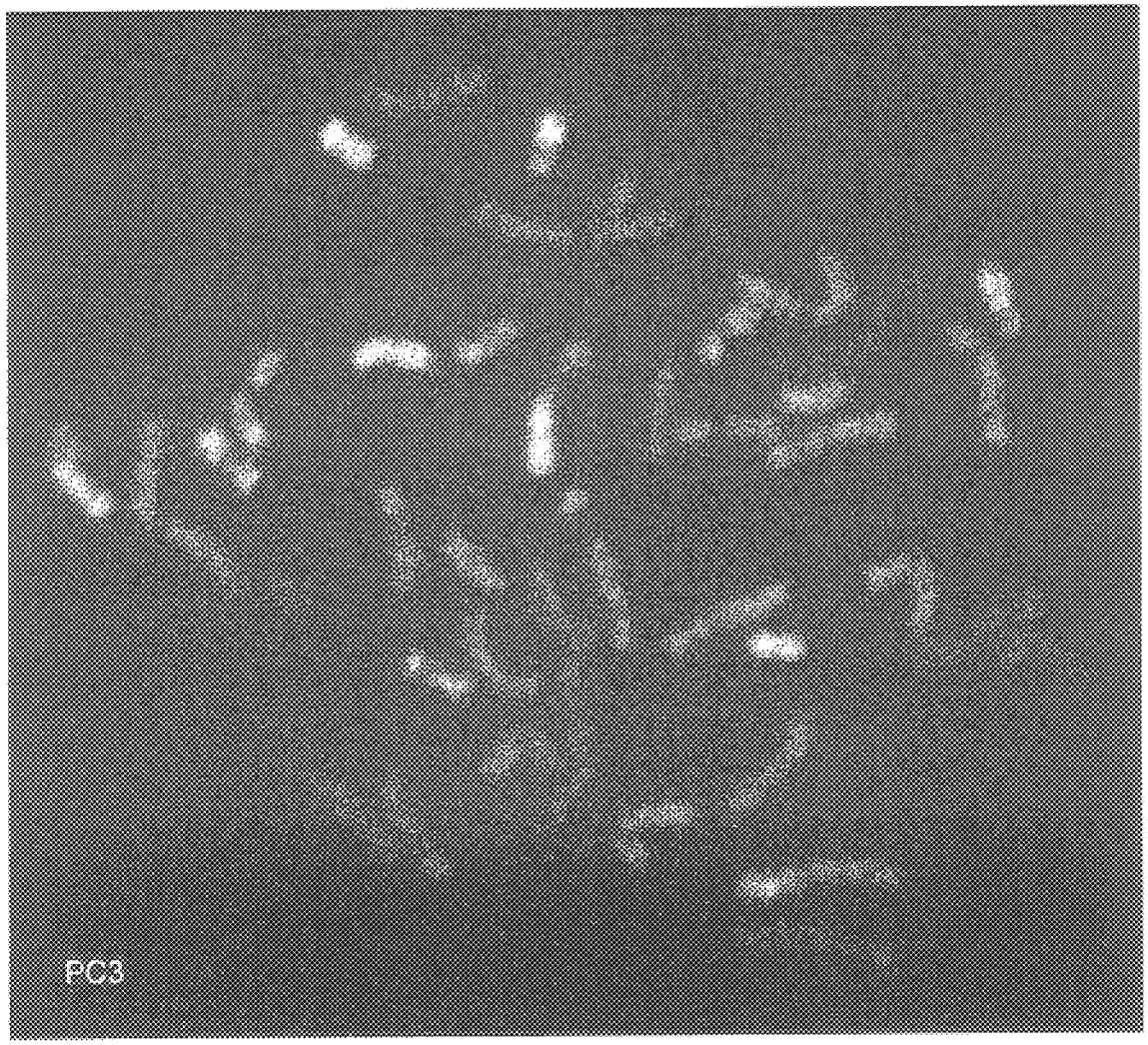
Figure 5D:
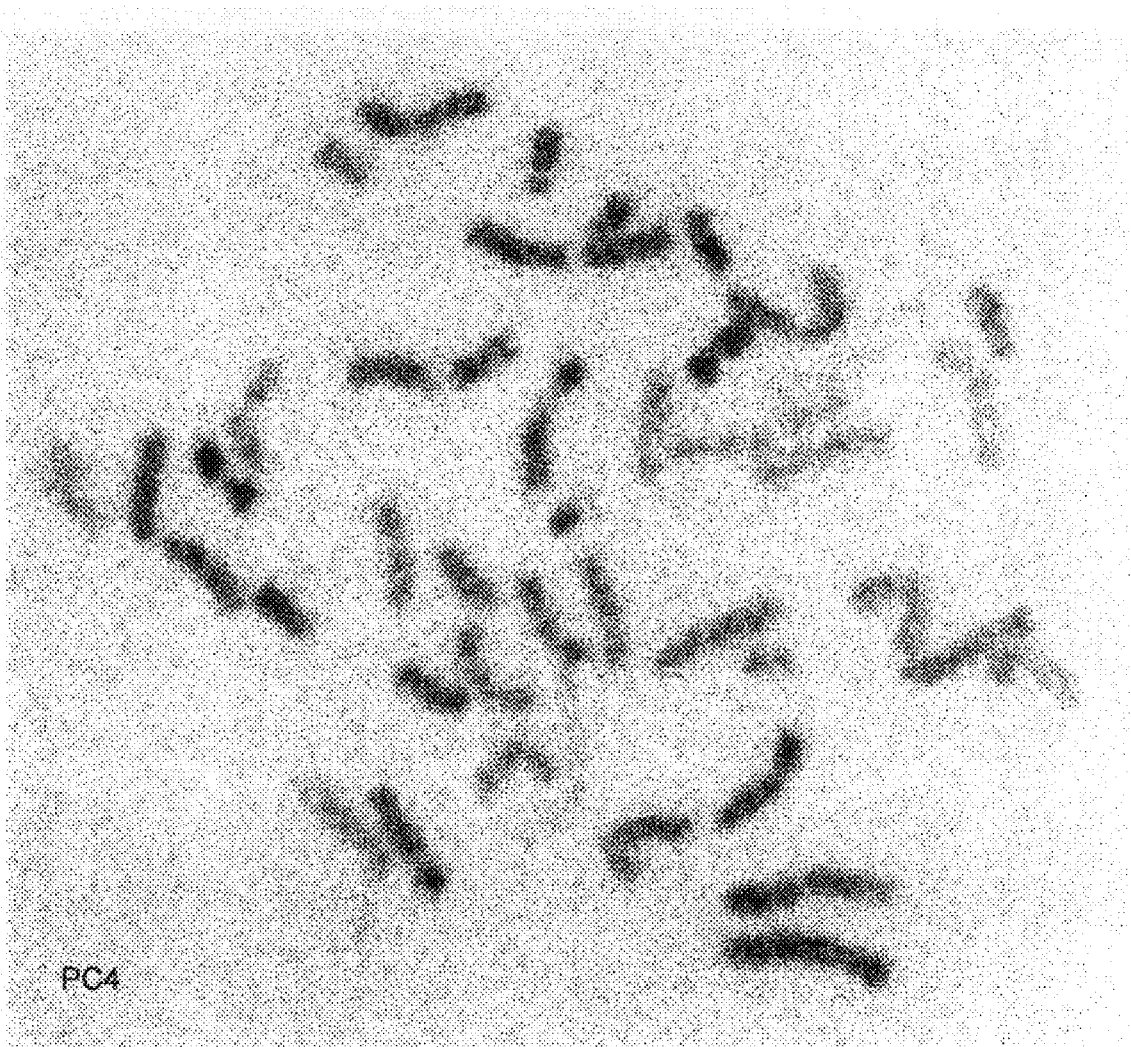
Figure 5E:
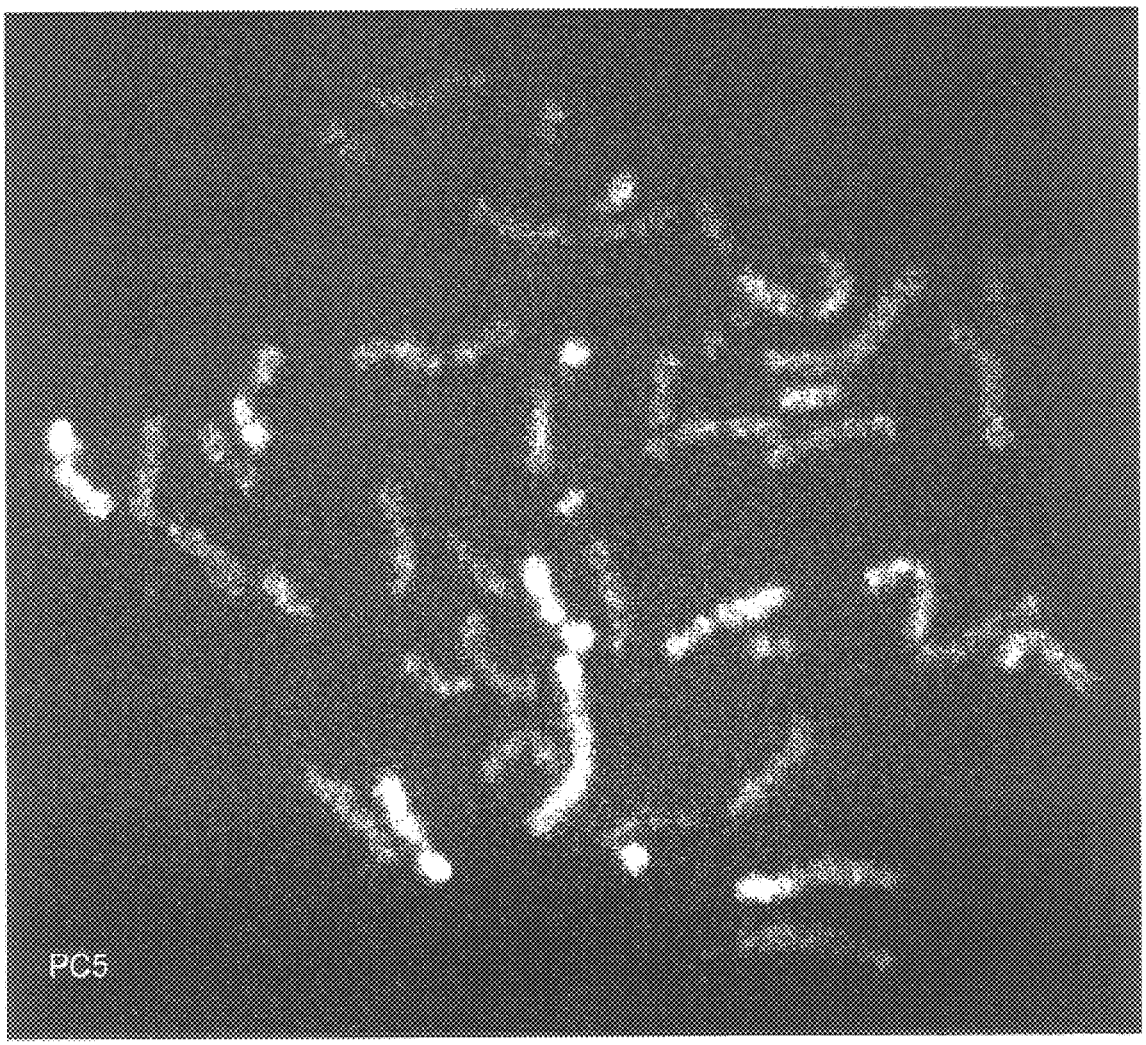

FIG. 4 presents 20 eigenvalues corresponding to these eigenvectors in decreasing order. Please note that this is a logarithmic display. From the graph presented in FIG. 4, one notices that the eigenvalues decrease very sharply with increasing number. From the point of view of the information content of the spectral cube, one can say that more than 95% of the information is contained in the first PCA image. On observing the PCA images, one notices that the chromosomes do appear only in the first 7 components, the first five of which are shown in FIGS. 5a–e.

Figure 6:
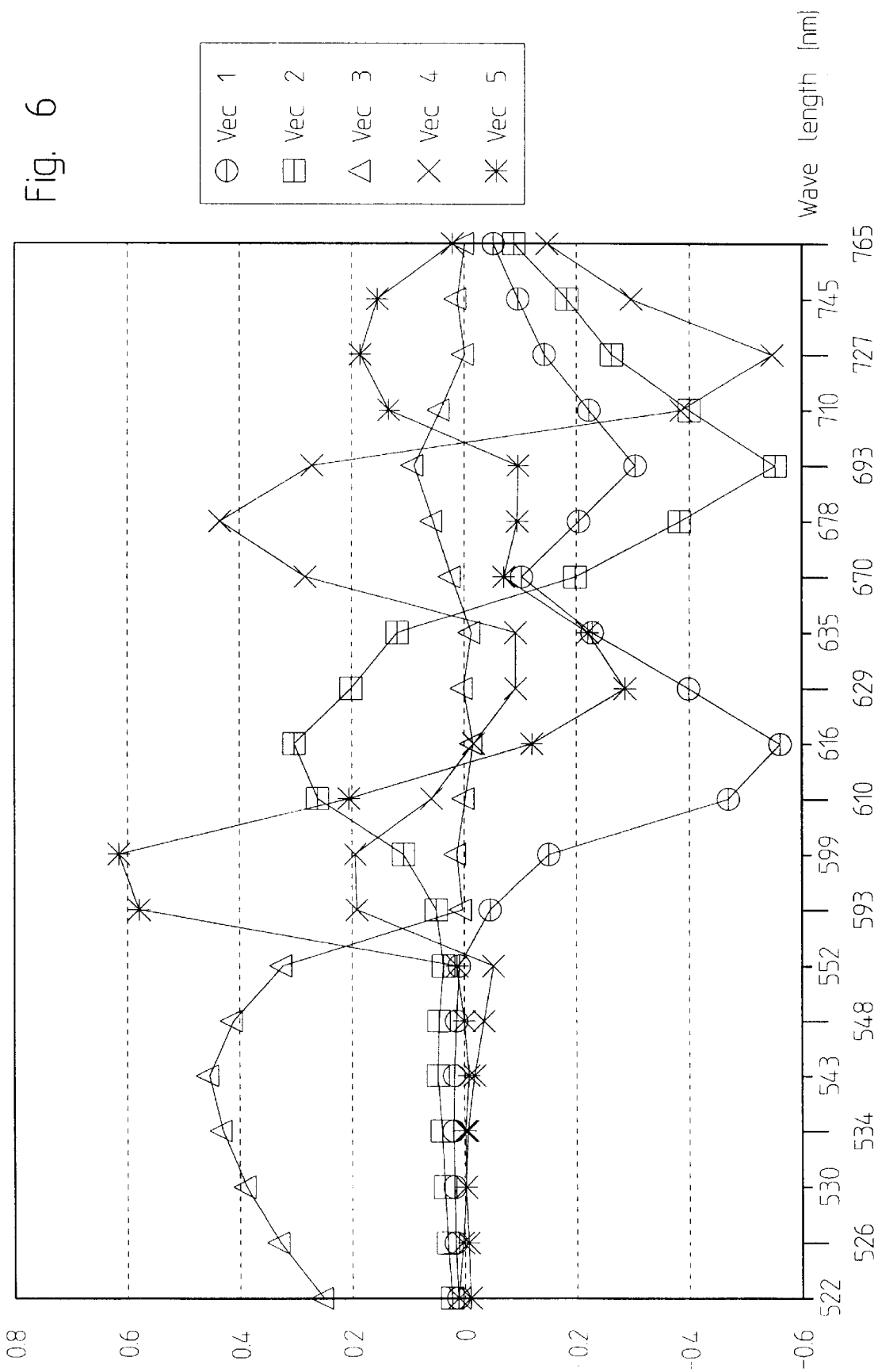
FIG. 6 is a graphic presentation of matrix V shown in Table 4.

Table 4 presents the first five (most significant) eigenvectors (Vec 1–Vec 5) for this system. Vec 1 being the most significant, whereas the first 20 lines of each column represent the relative weight of the wavelength depicted in the leftmost column. FIG. 6 is a graphic presentation of the first five vectors of matrix V.

TABLE 4

|        | Vec 1  | Vec 2  | Vec 3  | Vec 4  | Vec 5  |
|--------|--------|--------|--------|--------|--------|
| 522 nm | 0.012  | 0.023  | 0.251  | 0.011  | −0.010 |
| 526 nm | 0.016  | 0.030  | 0.328  | 0.003  | −0.007 |
| 530 nm | 0.018  | 0.035  | 0.388  | −0.003 | −0.003 |
| 534 nm | 0.019  | 0.040  | 0.430  | −0.006 | −0.002 |
| 543 nm | 0.018  | 0.047  | 0.454  | −0.018 | −0.008 |
| 548 nm | 0.014  | 0.045  | 0.411  | −0.035 | 0.000  |
| 552 nm | 0.009  | 0.037  | 0.323  | −0.052 | 0.013  |
| 593 nm | −0.046 | 0.050  | 0.003  | 0.191  | 0.579  |
| 599 nm | −0.151 | 0.108  | 0.013  | 0.194  | 0.615  |
| 610 nm | −0.470 | 0.261  | −0.002 | 0.058  | 0.205  |
| 616 nm | −0.562 | 0.303  | −0.016 | −0.017 | −0.121 |
| 629 nm | −0.399 | 0.201  | 0.001  | −0.092 | −0.286 |
| 635 nm | −0.228 | 0.119  | −0.013 | −0.092 | −0.220 |
| 670 nm | −0.103 | −0.198 | 0.022  | 0.283  | −0.071 |
| 678 nm | −0.204 | −0.383 | 0.055  | 0.435  | −0.095 |
| 693 nm | −0.304 | −0.553 | 0.089  | 0.271  | −0.096 |
| 710 nm | −0.222 | −0.400 | 0.042  | −0.385 | 0.134  |
| 727 nm | −0.143 | −0.262 | −0.001 | −0.548 | 0.185  |
| 745 nm | −0.096 | −0.183 | 0.012  | −0.297 | 0.154  |
| 765 nm | −0.052 | −0.089 | −0.001 | −0.148 | 0.021  |

The chromosome spectra in the decorrelated space, is calculated using Equation 5:

$$SS = S*V \quad (5)$$

wherein in the given example SS is a 24 by 20 matrix. It should be noted that, only N eigenvalues are of significance, typically 3–5, thus typically N is selected to be an integer greater than two. Consequently only about N (e.g., 3 to 5) out of the k (e.g., 20) numbers composing a line of SS in the given example are of any significance, additional eigenvectors and eigenvalues are of marginal significance and may therefore be discarded. In the following it is assumed that 5 (e.g., N=5) are significant, although a smaller number can be used.

Thus, a chromosome is uniquely specified by its N (e.g., 5) coordinates in the N-dimensional space with respect to the N chosen eigenvectors (and eigenvalues). These N coordinates represent the coefficients of the linear combination of the chromosome in question with respect to the N orthogonal eigenvectors. Using this type of analysis as compared with forming the matrix S for all the pixels in the cube (instead of only L mathematically manipulated pixels) ensures that (i) background pixels are not introduced into the calculation, and therefore the noise associated with them is avoided, and that (ii) each of the chromosomes is equally represented in terms of number of pixels. Table 5 presents an example of a truncated SS matrix. In this Table each row represents the projection of a given human chromosome on the five orthogonal eigenvectors or principal components (PCs) describing the spectral cube(s).

TABLE 5

|  | PC No. 1 | PC No. 2 | PC No. 3 | PC No. 4 | PC No. 5 |
|---|---|---|---|---|---|
| Chr. 1 | −0.637 | −0.200 | 0.132 | −0.002 | 0.110 |
| Chr. 2 | −0.204 | −0.145 | 0.075 | −0.090 | 0.068 |
| Chr. 3 | −0.407 | −0.012 | 0.205 | −0.053 | 0.118 |
| Chr. 4 | −0.521 | 0.051 | 0.074 | −0.003 | 0.091 |
| Chr. 5 | −0.329 | −0.258 | 0.193 | −0.053 | 0.079 |
| Chr. 6 | −0.748 | −0.374 | 0.139 | −0.079 | 0.090 |
| Chr. 7 | −0.432 | −0.249 | 0.117 | −0.003 | 0.098 |
| Chr. 8 | −0.229 | −0.107 | 0.105 | 0.006 | 0.065 |
| Chr. 9 | −0.387 | −0.041 | 0.139 | −0.030 | 0.088 |
| Chr. 10 | −0.285 | −0.073 | 0.072 | −0.052 | 0.122 |
| Chr. 11 | −0.317 | 0.020 | 0.121 | −0.021 | 0.065 |
| Chr. 12 | −0.306 | −0.281 | 0.107 | −0.062 | 0.066 |
| Chr. 13 | −0.782 | 0.067 | 0.276 | 0.002 | 0.112 |
| Chr. 14 | −0.430 | −0.510 | 0.131 | −0.002 | 0.060 |
| Chr. 15 | −0.293 | −0.107 | 0.273 | −0.111 | 0.092 |
| Chr. 16 | −1.180 | −0.519 | 0.175 | 0.010 | 0.093 |
| Chr. 17 | −0.244 | 0.040 | 0.186 | 0.005 | 0.102 |
| Chr. 18 | −0.726 | −0.271 | 0.290 | −0.013 | 0.077 |
| Chr. 19 | −0.311 | 0.069 | 0.057 | 0.014 | 0.117 |
| Chr. 20 | −0.261 | 0.010 | 0.381 | −0.034 | 0.086 |
| Chr. 21 | −0.782 | −0.109 | 0.125 | −0.120 | 0.101 |
| Chr. 22 | −0.581 | −0.462 | 0.145 | −0.046 | 0.158 |
| Chr. X | −0.686 | −0.011 | 0.087 | −0.070 | 0.107 |
| Chr. Y | −1.681 | 0.206 | 0.117 | −0.049 | 0.068 |

Collectively, the vectors of Table 5 form a reference template which may thereafter be used for classification of all the 24 chromosomes of a newly and similarly measured cube, as described hereinbelow in the following Examples.

Thus, for this example, given a measured spectrum (possibly background subtracted and averaged as described above) $M_i$, i=1–20, and a reference template of a set of eigenvectors $V_{ij}$, i=1–20 (wavelengths) j=1–5 (generally, i=1-k, whereas j=1–N), of which 1 is the most significant, then the five coordinates of $M_i$ in the five-dimensional space defined by the five PCs representing this spectrum are given by Equation 6:

$$P_k = \sum_{i=1}^{20} M_i V_{ik} \quad k = 1\text{-}5 \quad (6)$$

Each of these L (24 in the given example) N-dimension vectors (five-dimension vectors in the given example), P, is checked, by calculating the correlation, against the L template vectors, in order to decide to which chromosome type it belongs.

These L N-dimension vectors may then serve as attraction centers for classification as delineated hereinbelow.

It should be noted that when the term 'attraction center' is used herein it refers to a statistical method capable of attributing a pixel to a chromosome. Examples include but are not limited to (i) a minimum "distance" calculation in the N-dimensional space according to Equation 1, in which a "distance" is defined (for example the Euclidean definition or square root of the sum of the squares of the coordinate differences) and then the chromosome which is "closer" according to this definition is chosen, or (ii) a maximum correlation calculation in which the scalar products between the pixel vector and the L template vectors are calculated, and then the one that gives the highest result is chosen.

EXAMPLE 6

Classification

A preferred embodiment for classification of a new spectral cube is herein presented:

First, a 3×3 spatial averaging is performed, if required, as described above.

Second, the average spectrum of the whole cube, or the average spectrum of some, most or all the background pixels is calculated and is thereafter subtracted from the spectrum of each of the pixels in the cube, similar to as described above, if required.

Third, the spectrum of each pixel in the cube is projected onto the average spectra principal domain, which is, in the preferred embodiment the 10–15 or more, e.g., 40, preferably 20 dimension space of wavelengths or in other words the k spectral slices, to obtain an N dimension vector for each pixel. In a preferred embodiment, projection of the spectrum of each of the pixels is via the scalar product of the spectrum vector with the orthogonal base vectors of the PC space.

Finally, the correlation of each of the projected spectra with all of the L N-dimension vectors (24 5-dimension vectors in the given example), which serve as attraction centers as described under Example 5, is calculated, and the L N-dimension vectors which gives the highest correlation is chosen as the chromosome to which that pixel is attributed to.

For color presentation, pixels attributed to each of the L (24 in the given example) different chromosome types are given a different artificial color to yield to an L (24) color karyotype.

Figure 7:
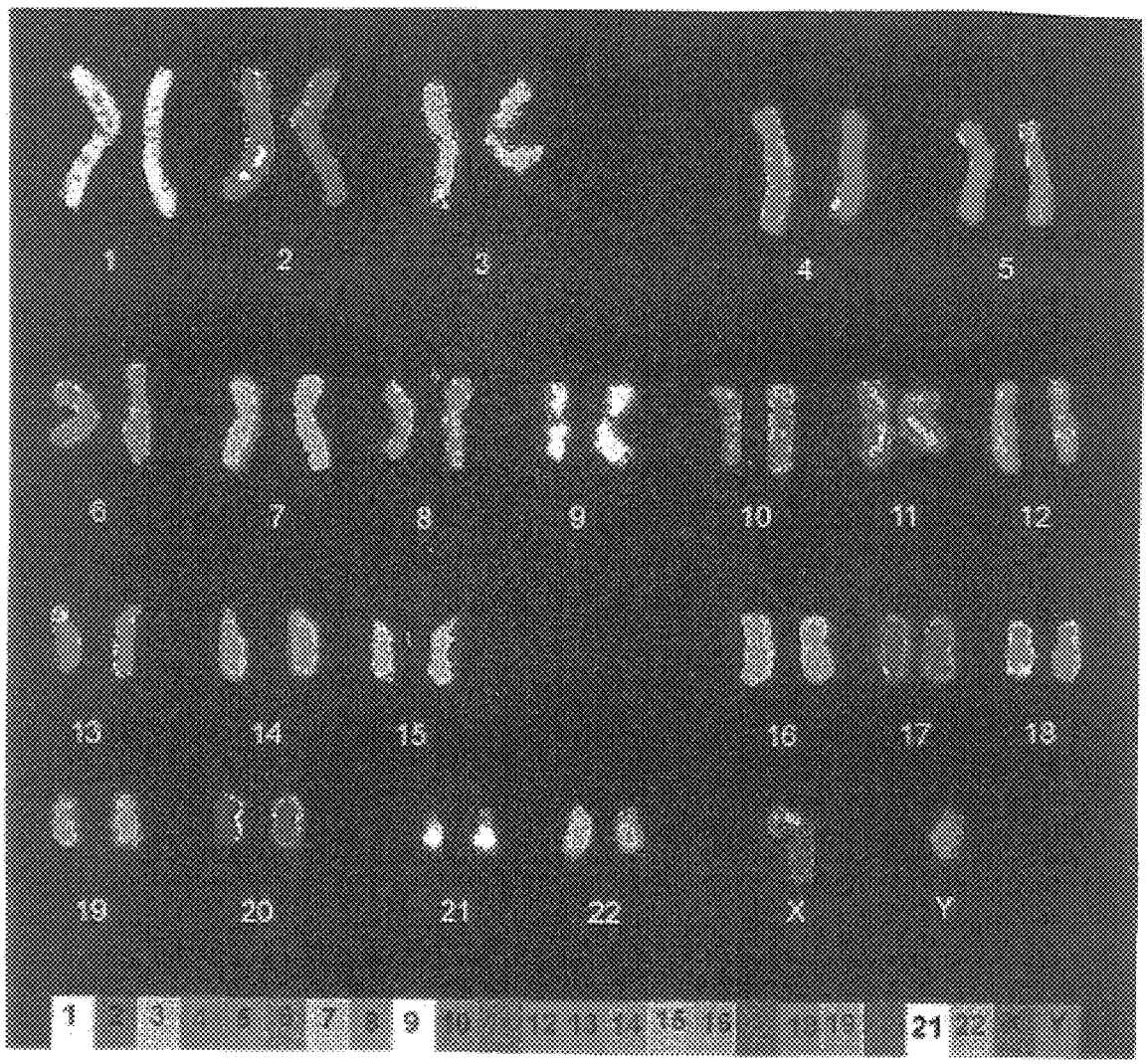
FIG. 7 is a male color karyotype obtained using the method of the present invention, wherein the first five PCs were used, the karyotype is arranged in chromosome pairs.

FIG. 7 presents such a color karyotype, wherein the 24 chromosome types are arranged in pairs. Further presented in FIG. 7 is a color key, according to which the chromosomes can be identified.

Figure 8A:
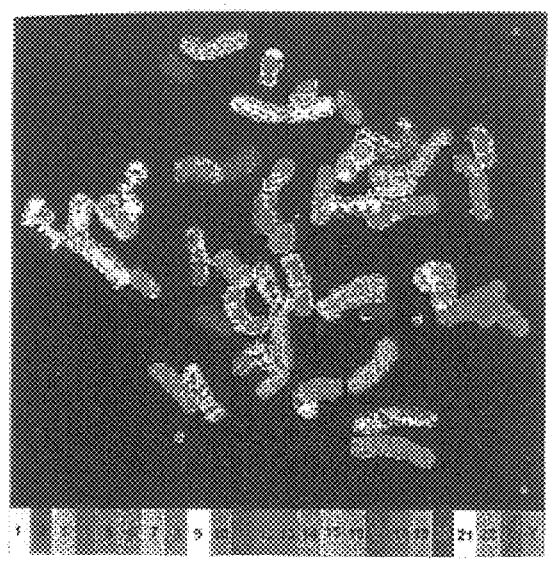
FIG. 8a–c are three male color karyotypes, prior to arrangement of the chromosomes in pairs, obtained using the method of the present invention, wherein the first three, four and five PCs were used, respectively.
Figure 8B:
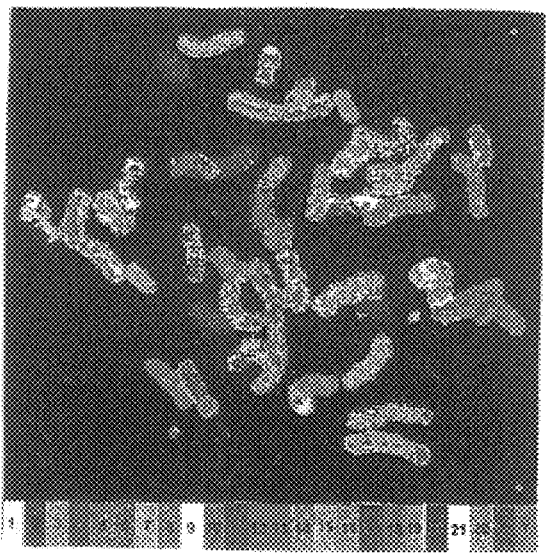
Figure 8C:
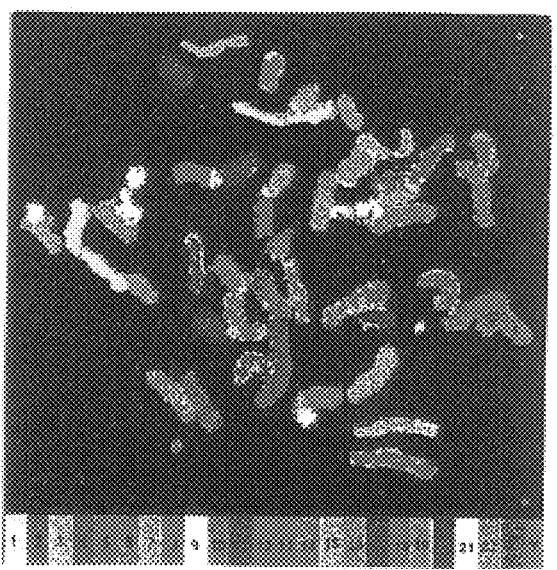

FIGS. 8a–c present color karyotyping results obtained using 24 N-dimension vectors, wherein N equals 3, 4 and 5, respectively. Please note that best results are achieved using 24 5-dimension vectors (FIG. 8c), yet, good results are obtained also with 24 4-dimension vectors (FIG. 8b). Furthermore, please note that using 24 3-dimension vectors as in FIG. 8a enables unambiguous color classification of most chromosome pairs. These results are not surprising considering the above mentioned fact that more than 95% of the information is contained in the first PCA image.

The classification approach of the present invention as herein described may be employed for various applications some of which are detailed hereinbelow. Following is a brief summary of likely applications of the classification approach of the present invention in the field of molecular cytogenetics. Two major fields of cytogenetics in which the classification approach of the present invention will have considerable impact with particular emphasis on diagnostic applications are: (i) clinical cytogenetics and (ii) tumor cytogenetics.

First, the classification approach of the present invention may be used for diagnostic purposes to detect chromosomal aberrations in for example cancerous cells, fetal cells, etc., in a fashion similar to as described in U.S. Pat. No. 5,817,462. About 400,000 cases in both clinical and cancer cytogenetics are analyzed each year in the United States alone, using conventional chromosome banding analysis. Chromosome painting using the classification approach of the present invention could be performed in addition to conventional banding analysis and would help to identify marker chromosomes that cannot be characterized using conventional banding alone. Acquired chromosomal aberrations are predominantly associated with malignant transformations. Roughly, two malignancies can be discerned: (i) hematological malignancies and (ii) solid tumors. Since the cells from hematological malignancies are easily cultured in vitro, the chromosome banding analysis of those tumors is one of the success stories in cytogenetic and genetic cancer research. Two well known examples include the identification of the Philadelphia chromosome in chronic lymphatic leukemia (CLL) and the a specific chromosomal aberration in Burkitt's lymphoma. Many more tumor specific chromosomal aberrations were described in hematological malignancies in the last decade and are used as a diagnostic and research tool. In many cases the delineation of a recurrent chromosomal aberration has allowed to identify on a molecular basis the mechanism of malignant transformation. Disturbingly, less is known in the field of solid tumors (such as breast, colon, brain lung and others tumors). This discrepancy is even more disturbing because solid tumors play a much higher role in human morbidity than hematological malignancies. The discrepancy is mainly due to technical difficulties common in solid tumor cytogenetics. Solid tumors cells are often difficult to culture, the chromosome preparations are of poor quality, preventing a high resolution cytogenetic analysis, and secondary chromosomal aberration, not necessarily related to tumor initiation or progression are a common feature of these tumors. The availability of a hybridization based chromosomal screening test (i.e., chromosome painting) fills in a methodological gap and is as described above desperately required. Partly, comparative genomic hybridization helps in this respect. However, structural chromosomal aberration cannot be detected and always displays as average of chromosomal aberration in a cell mixture. It is very likely to predict that hybridization based karyotyping would become a widespread method for the delineation of recurrent chromosomal aberrations in solid tumors, both in basic research and in the diagnostic laboratory.

Second, the classification approach of the present invention may be used for comparative cytogenetics [see, J. Weinberg and R. Stanyon (1995) Current opinion in genetics and development 5, 792–797], in a fashion similar to as described in U.S. Pat. No. 5,817,462, to detect and visualize chromosomal rearrangements which changed chromosome morphology during evolution. In the study of evolutionary related species and in the study of model systems (for example mouse as a model system for human) it is in many cases required to obtain comparative genome maps in which chromosomes of two or more species are aligned according to their sequence similarities and thus their chromosome-borne genetic information. Using the classification approach of the present invention will facilitate obtaining such comparative maps. Consider for example the preparation of a human-mouse chromosome comparative map. For this purpose a complete set of chromosome paints of one of the species (e.g., human) are to be simultaneously hybridized with chromosome spreads of the other species (mouse in the given example) and classified as described above. The result is an image of the mouse karyotype painted with the human chromosome paints. Thus, an alignment can be made between the karyotypes of the two species.

Third, the classification approach of the present invention may be applied to cells during interphase, mitosis or meiosis. For example, this classification approach may be used to detect interphase chromosome three dimensional arrangements. Little is so far known about the chromosome organization during interphase, yet it is reasonable to suspect that changes occur in the chromosome organization during interphase in malignant cells. Thus, the classification approach of the present invention may be of great value for early detection of various malignancies, defining the stage of a malignant disease, and hence better adjust a treatment to examined patients, etc. It should be noted that using the classification method of the present invention in combination with a three dimensional reconstruction means (e.g., a confocal microscope) may be used to extract three dimensional information of chromosome organization during interphase, mitosis or meiosis.

Fourth, many cancers and genetic disorders are characterized by chromosome deletions, translocations and other rearrangements and gross abnormalities (e.g., gene amplification). Using the classification approach of the present invention will enhance the ability to detect such abnormalities.

Fifth, one of the common chromosomal aberrations is associated with Down's-syndrome. It was long ago established that Down's syndrome is associated with trisomy of chromosome 21. More careful examination revealed that a specific region of chromosome 21 (21q22) is always associated (i.e., appears in trisomy) with this common syndrome. However, in some cases the karyotype of individuals affected with Down's syndrome is apparently normal as determined by conventional G- or R-banding karyotyping techniques. The widely accepted explanation to this phenomenon is that in these cases the trisomy is of a fragment derived from the 21q22 chromosome region which fragment is small and below the resolution of the conventional banding techniques. However, using the classification method of the present invention will enable to detect these so far undetectable chromosome 21 trisomies in embryonic cells obtained for example via chorionic villi sampling and to enable a more educated genetic counseling to high risk women. It should be noted that chromosome 13 and chromosome 18 or fragments thereof were also reported to appear in trisomies resulting in birth of strikingly abnormal children and that the classification method of the present invention can be similarly applied for a prenatal diagnosis of these devastating chromosome 13 or 18 trisomies.

Sixth, the classification method of the present invention, combined with the rapidly developing techniques of separating embryonic cells from peripheral blood of a pregnant woman will be of great value for low-risk prenatal karyotyping for the detection of chromosome 21 trisomies and other, less frequent chromosome abnormalities.

Seventh, the classification method of the present invention can be used for the generation of a multicolor banding pattern of chromosomes (i.e., bar-coding, multicolor banding karyotype). For details regarding chromosome bar coding the reader is referred to C. Lengauer et al. (1993) Hum. Molec. Genet. 5, 505–512. The first goal of the human genome project (HGP) is about to be completed. This goal is the generation of a physical map of the human genome. The term physical map refers to the cloning of the entire genome in large insert vectors such as YAC-clones or BAC-clones and the mapping of these clones by means of genetic, cytogenetic and physical mapping. Two major sources of human DNA were used for this endeavor, radiation hybrid cell lines and YAC-contigs that contain overlapping clones for all human chromosomes. The completion of this map allows to retrieve for virtually every region in the genome specific clones that are required to identify genes that are causally involved in inherited or acquired genetic diseases including cancer. By combining FISH with multiple YAC- or BAC-clones or radiation hybrids and spectral imaging it is possible to generate a multicolor banding pattern for all human chromosomes that will ultimately link the genetic and the cytogenetic map. As an example, consider the use of a radiation hybrid panel (Stanford panel) [see, Barret J. H. (1992) Genetic mapping based on radiation hybrids. Genomics 13, 95–103]. Each individual panel of the Stanford panel contains a set of DNA fragments with an average fragment size of ca. 5,000 kbp. Each individual panel covers ca. 20% of the human genome. The cohyhridization of fluorescent probes derived from five such panels would therefore result in coverage of most of the genome and thus labeling of all human chromosomes. However, the fragments are randomly distributed in the individual panels. Therefore, the number of panels that are required for a complete coverage of the human genome is higher (e.g., 6–10 panels). In the following description assumed is that five individual panels are used. The chromosome fragments of each of the panels are labeled with a different fluorophore (or a different combination of fluorophores, e.g., combinatorial labeling or hybridization strategies) by for example directly incorporating dUTP-conjugated fluorophores using primers derived from interspersed repetitive sequences (IRS, e.g., Alu sequences) in a method known in the art as IRS-PCR approach such as Alu-PCR, m which guarantees an exclusive amplification and labeling of human sequences only. If DNA from a species other than human is to be thus amplified and or labeled, a species specific interspersed repetitive sequence (IRS) characterizing the genome of that species is to be used to derive suitable PCR primers. A single separate hybridization of one of the individual panels would give a banding pattern of a chromosome spread in one color with a coverage of about 20% of the genome and an average band size of 5,000 Kbp. Due to the random overlap of individual chromosome fragments in the five hybrid panels, the cohybridization of five differentially labeled groups (each group is represented by a single panel) of fragments would result in a banding pattern including bands that have pure colors, bands that include a combination of two, three, four, as well as five colors each, collectively 31 possible color combinations, which combinations can be distinguished using spectral imaging. To this end, a preprocess for classification should be performed in a similar fashion to as described above to obtain, in the given example, 31 different N-dimension vectors, one for each of the 31 color combinations. Classification of new samples can then be performed essentially as described hereinabove. It is clear that describing 31 color combinations is for illustrative purposes only and that any other suitable number of combinations is included in the scope of the present invention. The generation of a multicolor high resolution banding pattern of chromosomes has two distinct advantages as compared to the use of chromosome painting probes (i.e., chromosome paints) as follows. Chromosome painting is a well suited tool to detect interchromosomal aberrations such as translocation or homogeneously staining regions as well as additional chromosomes material such as marker chromosomes or double minute chromosomes. Intrachromosomal aberrations such as deletions and duplications would be detected only if the size of the aberrations affect the length of the chromosomes, whereas chromosomal inversions are not detectable at all by this method. However utilizing a multicolor banding pattern, inter- as well as intrachromosomal aberrations could be diagnosed because they would affect the sequence of the chromosomal bands. One major advantage of multicolor high resolution banding pattern using pre-mapped DNA fragments (e.g., YAC-clones and radiation hybrids cell lines) is the possibility to integrate the genetic and the cytogenetic map. Each multicolor band is characterized by a specific set of sequence tagged sites. These are PCR products that occur only once in the genome. Following is a description of the usefulness of the integrated cytogenetic and genetic map. For example, the lack of a specific color band on a chromosome derived from a tumor cell is indicative of a microdeletion that often reflects the loss of a tumor suppressor gene. The knowledge of the sequence target sites (STS's) that are specific for this band would allow to screen any large insert clone collection and retrieve a number of specific clones that are highly likely to contain the gene that is deleted in the described example. It should be mentioned that with the large scale sequencing efforts now underway and with the integration of expressed tagged sites (loci that are known to contain a gene) the value of a hybridization based multicolor banding pattern would increase even more. It is also conceivable that such a multicolor banding pattern could be readily automated. Despite considerable efforts automation of cytogenetic diagnosis based on conventional chromosome bands was so far not successful. The approach described hereinabove will not only be applicable for the generation of a hybridization based banding pattern of human chromosomes but also for other mammalian (e.g., mouse) and non-mammalian species. This will be particularly useful for the analysis in animal models of human diseases including cancer. In analogy to the scenario described for the radiation hybrid panels, a multicolor banding pattern for all human chromosome could be achieved by cohybridization of a set on individual large insert clones such as YAC-clones, Pl-clones, BAC-clones or, depending on the resolution that is desired the use of contigs (overlapping clones) from these sources. In further analogy to the use of radiation hybrid panels, a multicolor banding pattern could be introduced by deliberately labeling overlapping clones or contigs with different fluorophores. All advantages of the hybridization based chromosome banding approach has as compared to the use of chromosome paints or to conventional chromosome banding described above, applies to usage of large inserts clones as well. It will be appreciated by one ordinarily skilled in the art that the retrieval of clones involved in chromosome breakpoints or in chromosomal deletion would be even more straightforward than with the use of radiation hybrid panels. Another source of chromosome fragments suitable for use for multicolor chromosome banding are fragments obtained by microdissection of chromosomes. Microdissected chromosomes fragments are generated by manual or laser micromanipulation of chromosome spreads as well known in the art. The fragments thus produced are typically multiplied by polymerase chain reaction using for example degenerated oligonucleotides primers (DOP) in a method known in the art as DOP-PCR, or using primers derived from interspersed repetitive sequences (IRS, e.g., Alu sequences) in a method known in the art as IRS-PCR. Yet, an additional source of chromosome fragments suitable for use for multicolor chromosome banding are fragments generated by DNA restriction approaches that generate large DNA fragments and electrophoresis approaches capable of size separating large DNA fragments. As far as generating large DNA fragments by DNA restriction two approaches may be considered. According to the first, a partial digestion by an endonuclease (e.g., frequent or rare cutter) is used, whereas according to the second, a complete digestion by a rare cutter endonuclease (e.g., NotI), is used. The latter is presently preferred, since a complete digestion can be repeated to yield identical results in independent trials, whereas partial digestion is random in nature. Electrophoresis approaches capable of size separating large DNA fragments are well known in the art and include pulse field gel electrophoresis (PFGE). Thus, for example, extracting DNA from consecutive regions along a PFGE lane, labeling the DNA extracted from each of the regions using a different fluorophore and cohybridizing thus formed probes to chromosomes, would result in a multicolor banding pattern of the chromosomes similarly to as described above. Large DNA fragments may additionally be obtained via gradient centrifugation such as sucrose or cesium chloride gradients as well known in the art. Nevertheless, it will be appreciated that using these approaches do not provide a possibility to integrate the genetic and the cytogenetic map as described above and is therefore presently less favorable. The generation of a multicolor banding pattern of chromosomes (i.e., multicolor banding karyotype) based on fluorescent in situ hybridization and the classification approach of the present invention can be used for various practical applications. These include for example (i) screen for chromosomal aberrations using for example specifically tailored clone sets; (ii) screening for telomeric deletions, which are otherwise difficult of detection; (iii) screening for chromosomal aneuploidies during prenatal diagnosis; (iv) screening for recurrent chromosomal breakpoints; (v) multicolor comparative genomic hybridization; (vii) combining multicolor FISH with other measurements of cytological and immunohistochemical stains for multiparameter analysis of tumor cells; (viii) combining multicolor banding patterns with conventional R- or G-bands; (ix) analysis of genetic aberrations directly in interphase cells; and (x) screening for chromosomal aberrations in radiation or mutagen exposed populations.

Eighth, the classification approach of the present invention can be expanded to include a morphological algorithm, as well known in the art of automatic karyotyping, to achieve even better results.

EXAMPLE 7

Decorrelation Matched Optical Filters

In the following paragraphs, described is the possibility of utilizing a small number of predetermined optical filters, referred herein as decorrelation matched filters or matched filters, in order to classify chromosomes using their fluorescent spectra, after a specific chromosome staining protocol is applied.

This new concept is based on the above described work using data from a spectral cube and a decorrelating statistical analysis such as principal component analysis, for data reduction.

After the chromosome staining technique is applied, each chromosome possesses a specific spectra. Thus chromosome classification is performed by matching the spectra to a predetermined template which is derived using for example PCA.

However, the nature of these specific spectra is such that there is a strong correlation among them all. Applying the PCA, which is one of the existing decorrelation techniques available, reveals that the chromosome specific spectra are linear combinations of a small number of "basis" spectra, the principal components or eigenvectors of the covariance matrix. The number of "basis" spectra being somewhere between 3 and 5. Consequently, the measurement and data analysis can be simplified by using specific hardware rather than imaging spectroscopy.

The construction of the specific hardware according to the present invention is as follows. Spectral imaging spectroscopy and decorrelating statistical analysis are utilized, as described above, to calculate the reference vectors and template.

According to the present invention, the P N-dimension vectors, wherein N is an integer greater than two, e.g., three or five, for each pixel of the image, can be measured directly, using imaging microscopy and N pre-designed filters.

Observing Equation 6, defining the P vector, one realizes that it represents, mathematically at least, a filtration of the spectrum M. Physically it is not filtration as V has negative values as well. This problem however can be solved by a simple mathematical manipulation as follows:

Equation 7 defines a physical filter F (representing transmission in the range 0–1):

$$F_{ik} = \frac{V_{ik} - V_{ik\min}}{V_{ik\max} - V_{ik\min}}, \quad k = 1\text{-}N \tag{7}$$

where $V_{ik\ min}$ equals minimum ($V_{ik}$) over all i, and $V_{ik\ max}$ equals maximum ($V_{ik}$) over all i.

There are of course N such filters (one for each k), wherein N is an integer greater than two, e.g., three or five. These N filters are physically realizable.

Using these filters, each pixel in the image can be measured to produce an N-dimension vector for each.

A pixel whose spectrum is $M_i$ i=1–20, will produce a PP N-dimension vector described by Equation 8:

$$PP_k = \sum_{i=1}^{20} M_i F_{ik}, \quad k = 1\text{-}N \tag{8}$$

One observes that the PP vectors and the P vectors are connected and the P vector can be calculated using Equation 9:

$$P_k = \Sigma M_i V_{ik} = (V_{ik\ max} - V_{ik\ min}) PP_k + V_{ik\ min} \Sigma M_i \tag{9}$$

All the components of the V vectors are known from the stage of reference template preparation described hereinabove under Example 5. Table 6 represents the minimum and maximum value of the eigenvectors shown in Table 4 above. The sum $\Sigma M_i$ is the intensity of the pixel under discussion, which is measured directly from the microscope (no filter used).

TABLE 6

|     | Vec 1  | Vec 2  | Vec 3  | Vec 4  | Vec 5  |
|-----|--------|--------|--------|--------|--------|
| min | −0.562 | −0.553 | −0.016 | −0.548 | −0.286 |
| max | 0.019  | 0.303  | 0.454  | 0.435  | 0.615  |

Figure 9:
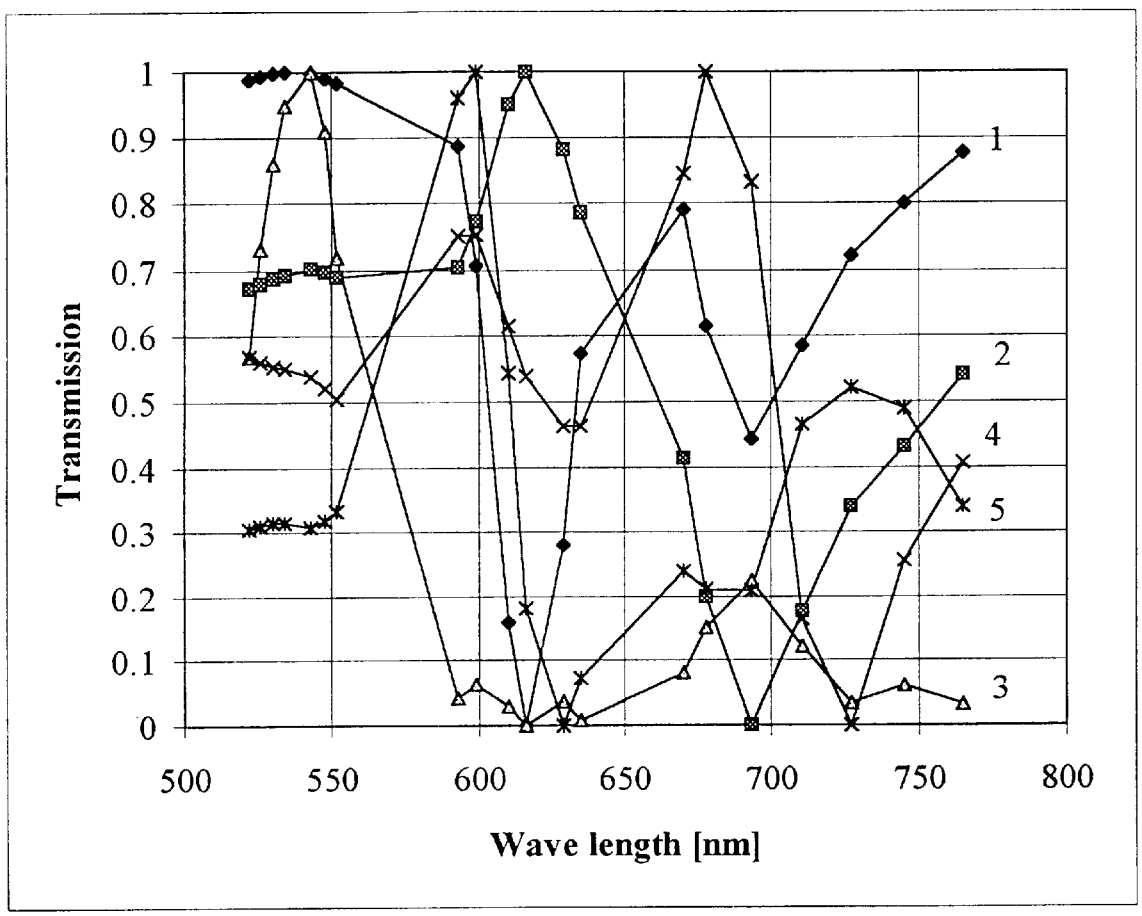
FIG. 9 is a graphic presentation of five decorrelation matched filters as calculated using the data in Tables 4 and 6 and Equation 7, according to the present invention.

FIG. 9 graphically depicts five decorrelation matched filters as calculated using the data in tables 4 and 6 and Equation 7.

Thus, by imaging painted chromosomes N+1 times, six in the given example, once for each filter (there are N such filters) and once without any filter and using Equation 9, one can calculate the P N-dimension vector for each pixel in the image. These vectors are then used for classification by employing the pre-prepared reference template, similarly to as described above under classification. As before, for color presentation, pixels attributed to each of the 24 different chromosome types are given a different artificial color to yield a 24 color karyotype.

The above described calculation of the physical filters is presently preferred. Yet, it will be appreciated by one ordinarily skilled in the art that in specific cases different calculations to limit the filters to the full dynamic range of 0–1, or to a segment of the full dynamic range (e.g., 0.1–0.9), are also possible. Furthermore, as each of the PCs shown in the graph of FIG. 6 has at least one positive section and at least one negative section, each of these PCs may be represented by two or more physical filters in which one or some filters represents the positive section(s) of the PC and the other(s) represent the positive magnitude of the negative section(s) of the same PC. It should be further noted that some PCs may have only positive or only negative values. In this case, they may be represented accordingly by one or more filters which represent the positive values of the PC, or, one or more filters which represent the positive magnitude of the negative values of the PC, respectively. In any case, a measurement using these filters can be performed and the P N-dimension vector for each pixel can be determined and used for classification similarly to as described above.

In addition, any of the filters presented in FIG. 9, or any other filters differently calculated, for example as described above, may be manufactured as a single filter, alternatively as a subset of few filters, which collectively, when sequentially applied for measurement, yield otherwise substantially identical results. It should thus be noted that when the term decorrelation matched filters is used herein and especially in the claims section below, it refers to all the possible options of calculating and manufacturing these filters, unless otherwise is specifically indicated.

It will be appreciated by one ordinarily skilled in the art that using the decorrelation matched filters according to the present invention is benefactory for all the cytogenetic applications based on the classification approach of the present invention as delineated under Example 6 above, especially for chromosome banding analysis.

EXAMPLE 8

Decorrelation Matched AOTFs and LCTFs

Tunable filters (TFs), such as acousto-optic tunable filters (AOTFs) and liquid-crystal tunable filters (LCTFs), are solid state electronically tunable spectral bandpass selectors having no moving parts which can be electronically tuned to any particular wavelength, as well known in the art. As such, a tunable filter can be thought of a variable bandpass filter that can be electronically tuned to any wavelength over its range.

A liquid-crystal tunable filter (LCTF) is a solid state electronically tunable spectral bandpass filter typically made of high molecular weight organic substances having a dipole. Tuning LCTF is performed by subjecting the liquid crystal to varying electrical voltages. LCTF is a birefringent filter that uses phase retardation to create constructive and destructive interference. By stacking a number of stages in series, a single bandpass is obtained in a manner similar to that of a multicavity interference filter. LCTF technology was introduced by Cambridge Research & Instrumentation (CRI) Inc. in 1992. The first generation LCTFs produced suffered various limitations as far as bandpass width and shape and transmission of polarized and especially of randomly-polarized light are concerned. However, second generation LCTFs have overcome these problems, enabling transmission of about 100 percent of polarized light, substantially greater than 50 percent of randomly-polarized light, broad bandpass (top and bottom) of variety of shapes in the spectral range of 400 nm to 720 nm. To the development in LCTFs the reader is referred to Clifford Hoyt (1996) Liquid crystals tunable filters clear the way for imaging multiprobe fluorescence. Biomotonics International, 3(4), 49–51. Further information concerning LCTF can be found in for example Hoyt and Benson (1992) Merging spectroscopy and digital imaging enhances cell research. Photonics Spectra 26(11), 92–97; Kopp (1994) Tunable birefringent filters using liquid crystal variable retarders. Proc. SPIE 2265, 192–201; Miller and Hoyt (1995) Multispectral imaging with a liquid crystal tunable filter. Proc. SPIE 2345, 354–365; and Koenig et al. (1994) In-vivo fluorescence detection and imaging of porphyrin-producing bacteria in the human skin and in the oral cavity for diagnosis of acne, caries, and squamous cell carcinoma. Proc. SPIE 2135, 129–138, all are incorporated by reference as if fully set forth herein.

Thus, the physical filters of FIG. 9 can be implemented by a single LCTF, which can be tuned at different times to implement a filter of any bandpass of any desirable shape.

An acousto-optic tunable filter (AOTF) is a solid state electronically tunable spectral bandpass filter which can be operated from the ultra violet through the visible and into the infrared regions of the optical spectrum. The AOTF operates on the principle of acousto-optic interaction in an anisotropic medium. In other words the AOTF functions by the interaction of light with traveling acoustic wave through the medium, which creates a periodic modulation of its index of refraction by means of the elasto-optic effect. This modulation acts as a three-dimensional sinusoidal phase grating for light incident upon the crystal, leading to the diffraction of certain wavelengths at an angle from the incident beam radiation. To this end, an acoustic transducer, typically a piezoelectric motor, is bonded to one face of the crystal and an acousto absorber is typically bonded to an opposite face. The transducer converts a high frequency rf (radio frequency) signal into a sinusoidal pressure wave which propagates laterally through the crystal. As a result, the medium operates similar to a grating, wherein incident light is diffracted to its spectral wavelengths, light of varying wavelengths is acquired different angles with respect to the incident light beam when leaving the medium as a throughput. The acoustic absorber at the opposite end of the crystal eliminates acoustic reflections which would corrupt the primary acoustic wave form. The conservation of momentum between the incident and diffracted photon wave vectors and the acoustic wave vector determines the wavelength of the diffracted light passing the medium at a given angle. Thus, without moving the AOTF, one can control the wavelength of light that will pass the medium in a selected angle. Optical tuning, or in other words the wavelength of light which passes the medium in a preselected angle, is achieved by selecting the rf frequency signal.

The use of AOTFs for spectroscopic applications and for spectral imaging applications is not new, see for example U.S. Pat. Nos. 5,216,484 to Chao et al., 5,377,003 to Lewis et al. Further information concerning the operation of AOTFs can be found in for example Wang and Lewis (1996) Acousto-optic tunable filters and their application in spectroscopic imaging and microscopy. In, "Fluorescence Imaging Spectroscopy and Microscopy". Feng, Wang and Brian, Eds. John Wiley and Sons Inc.; Harris et al. (1969) Acousto-optic tunable filters. Journal of the optical society of America, 59, 744–747; Chang (1977) Noncolinear acousto-optic filter with large angular aperture. Applied Physics Letters, 25, 370–372; Eliot et al. (1996) Imaging acousto-optic tunable filter with 0.35-micrometer spatial resolution. Applied Optics, 35, 5220–5226; and in U.S. Pat. Nos. 3,679,288; 3,944,334; 3,944,335; 3,953,107; 4,052,121; 4,342,502 and 5,039,855, all are incorporated by reference.

Traditionally AOTFs were used to generate a varying narrow bandpass, Nevertheless, electronically controlling the acouso wave parameters by for example supper imposition (e.g., linear combination) acoustic waves of different wavelengths and/or different amplitudes, by for example employing more than one transducer, enables to select any desired wave pattern that results in passing different intensities of light at variable wavelengths in a preselected angle. Furthermore, by omitting the acouso absorber to allow the presence and therefore superposition of waves reflected from the end face of the crystal can also be used to control passage of different intensities of light at variable wavelengths in the preselected angle. Thus, when driven with multiple closely spaced rf's, the AOTF also provides electronically variable bandpass and shape control. To this effect the reader is referred to Eliot et al. (1996) Imaging acousto-optic tunable filter with 0.35-micrometer spatial resolution. Applied Optics, 35, 5220–5226.

As a result, the physical filters of FIG. 9 can be implemented by a single AOTF, which can be tuned at different times to implement a filter of any bandpass having any desirable shape.

As stated above, any of the filters presented in FIG. 9, or any other filters differently calculated, for example as described above in Example 7, may be manufactured as a single filter, alternatively as a subset of few filters, which collectively, when sequentially applied for measurement, yield otherwise substantially identical results. Any such combination of filters may be implemented by a single tunable filter (LCTF or AOTF) which can be tuned at a different bandpass and shape to sequentially implement any of the filters. Thus, when the term decorrelation matched filters is used herein and especially in the claims section below, it refers to these options as well.

It will be appreciated that by using tunable filters such as AOTF and LCTF, a single filter is required for measurement, the tunable filter is tuned to change its spectral characteristics in a manner that sequentially follows any desired characteristics. Thus for measurement of in situ hybridized chromosomes according to a given experimental procedure, tuning information is selected such that the tunable filter sequentially implements decorrelation matched filters. This, however implies that the measurement involves no moving parts as it is electronically controlled.

It will be appreciated by one ordinarily skilled in the art that using the tunable filter based decorrelation matched filters according to the present invention is benefactory for all the cytogenetic applications based on the classification approach of the present invention as delineated under Example 6 above, especially for chromosome banding analysis.

EXAMPLE 9

A Spectral Decorrelation Measurement Apparatus Based on Decorrelation Matched Optical Filters As described above, for a given experimental protocol, e.g., given types of fluorophores and/or combinations thereof, a set of N (e.g., three to five) decorrelation matched filters can be calculated and manufactured. These filters can be used for fast collection of decorrelated projection of each pixel spectrum in a field of view onto a number of orthogonal PCs, provided that the observed object is treated according to the experimental protocol employed for calculating the transmittance function of the filters. These N values, collectively form an N-dimension vector for each pixel. Each of these vectors is then compared to reference vectors forming a reference template for classification as described above, and, based on this comparison, each pixel is attributed to a chromosome type and for presentation given a specifying artificial color.

Figure 10:
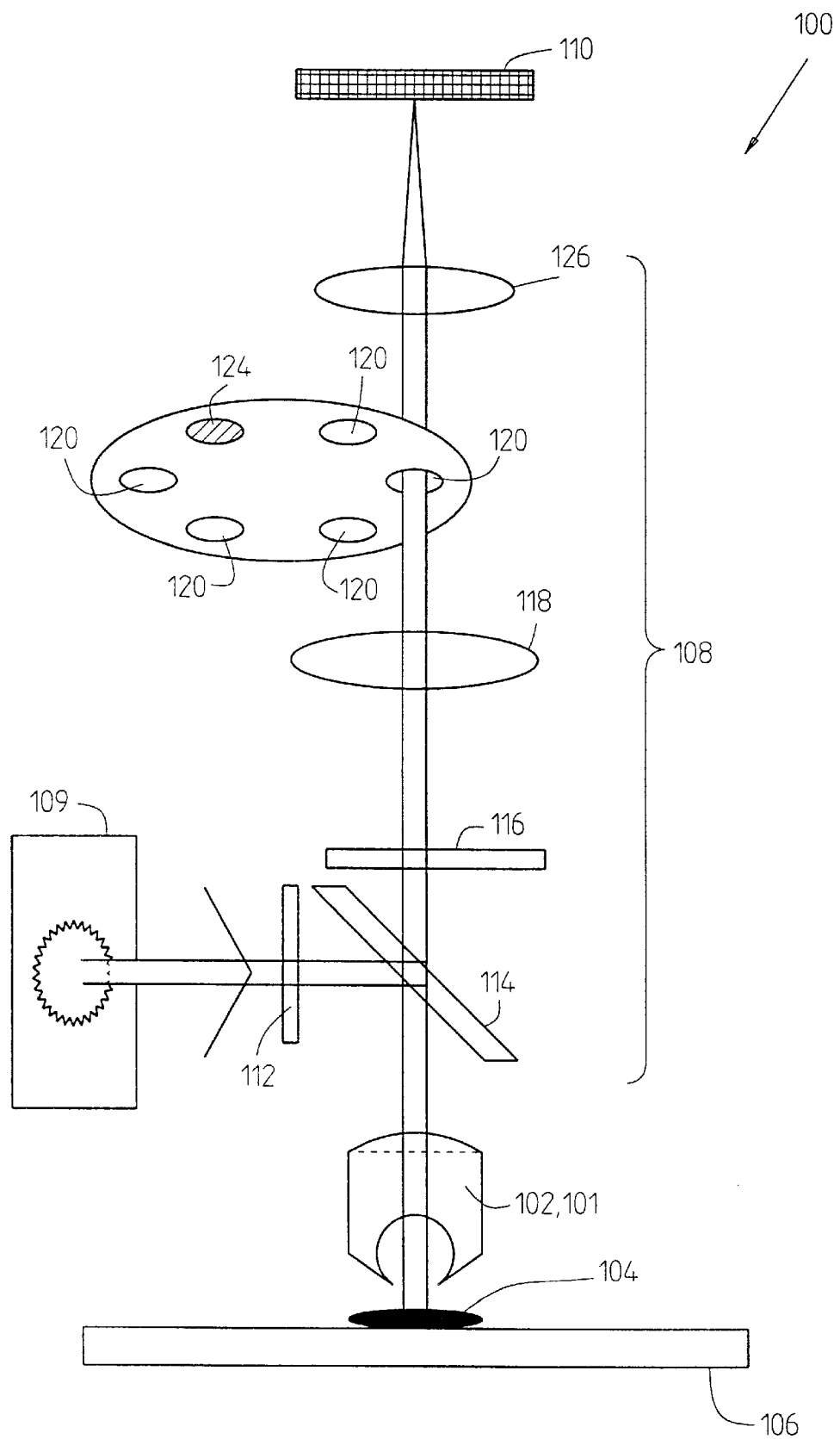
FIG. 10 is a schematic depiction of a filter wheel including spectral decorrelation measurement apparatus according to the present invention.

With reference now to FIG. 10. For ease of measurement, the N decorrelation matched filters are placed in an apparatus referred hereinbelow as a spectral decorrelation measurement apparatus or apparatus 100. Apparatus 100 is connected to a microscope 101, which is indicated by its objective lens 102. A sample of in situ painted chromosomes 104 to be analyzed is placed under microscope 101, on a supporting plane 106. Apparatus 100 further includes an optical system 108, which is for transmitting excitation light from light source 109 to sample 104 and emission light from sample 104 onto a detector 110, typically a two dimensional CCD array.

In a preferred embodiment, optical system 108 includes an excitation filter 112, which is placed in the path of light emitted from light source 109. Excitation filter 112 is capable of transmitting light in the range required for excitation of the fluorophores in sample 104, e.g., in the ultraviolet and blue ranges, and of blocking light in the range of fluorescent emission. Optical system 108 further includes a dichroic filter 114, typically a triple dichroic filter, for directing exiting light from filter 112 to sample 104 and emission light from sample 104 to detector 110. Preferably, optical system 108 further includes a barrier filter 116 for blocking any residual photons which are not in the spectral range of the emitted fluorescence. Depending on the type of microscope 101 employed, optical system 108 may further include a collimating lens 118 to ensure full collimation of the light. However, as well known in the art, some microscopes include a collimating lens themselves. In these cases collimating lens 118 may be discarded.

Optical system 108 further includes N (N is an integer greater than two, preferably N is in the range of 3–5) decorrelating matched filters 120, five of which are shown in FIG. 10, peripherally arranged on a rotatable filter carrying element 122, such as a filter wheel. Each of decorrelating matched filters 120 is designed as described hereinabove under Example 7. Rotatable filter carrying element 122 also includes one position 124 through which light passes undisturbed. The number N of decorrelating matched filters 120 may vary as described above and is determined by the number of eigenvalues or PCs employed to construct the reference vector for each of the chromosomes, or, in other words, the reference template.

Optical system 108 further includes a focusing lens for focusing light after passage through rotatable filter carrying element 122 onto detector 110.

The operation of apparatus 100 is as follows. Decorrelating matched filters 120 of rotatable filter carrying element 122 are kept successively in the light beam while detector 110 builds an images for each. That is to say that detector 110 builds an image with first filter 120, then rotatable filter carrying element 122 rotates to present another filter 120, and detector 110 starts building a new image in synchronization, and so on until one image for each filter 120 has been measured. One additional image is formed while position 124 through which light passes undisturbed is positioned in the path of light.

Using the data thus collected, Equation 9 above and the data in tables 4 and 6, the coordinates of the P N-dimension vector for each pixel are calculated in the N-dimensional space of the N PCs. These coordinates are then used for classification by employing the pre-prepared reference template, similarly to as described above under classification. As before, for color presentation, pixels attributed to each of the 24 different chromosome types are given a different artificial color to yield a 24 color karyotype.

It will be appreciated by one ordinarily skilled in the art that using apparatus 100 according to the present invention is benefactory for all the cytogenetic applications based on the classification approach of the present invention as delineated under Example 6 above, especially for chromosome banding analysis.

EXAMPLE 10

A Spectral Decorrelation Measurement Apparatus Based on Decorrelation Matched AOTFs and LCTFs As described above in Example 9, for a given experimental protocol, e.g., given types of fluorophores and/or combinations thereof, a set of N (e.g., three to decorrelation matched filters can be calculated and implemented by electronically tuning a tunable filter such as an AOTF or LCTF. Any of these filters can be used for fast collection of decorrelated projection of each pixel spectrum in a field of view onto a number of orthogonal PCs, provided that the observed object is treated according to the experimental protocol employed for calculating the transmittance function of the filters as implemented by tuning. These N values, collectively form an N-dimension vector for each pixel. Each of these vectors is then compared to reference vectors forming a reference template for classification as described above, and, based on this comparison, each pixel is attributed to a chromosome type and for presentation given a specifying artificial color.

Figure 11:
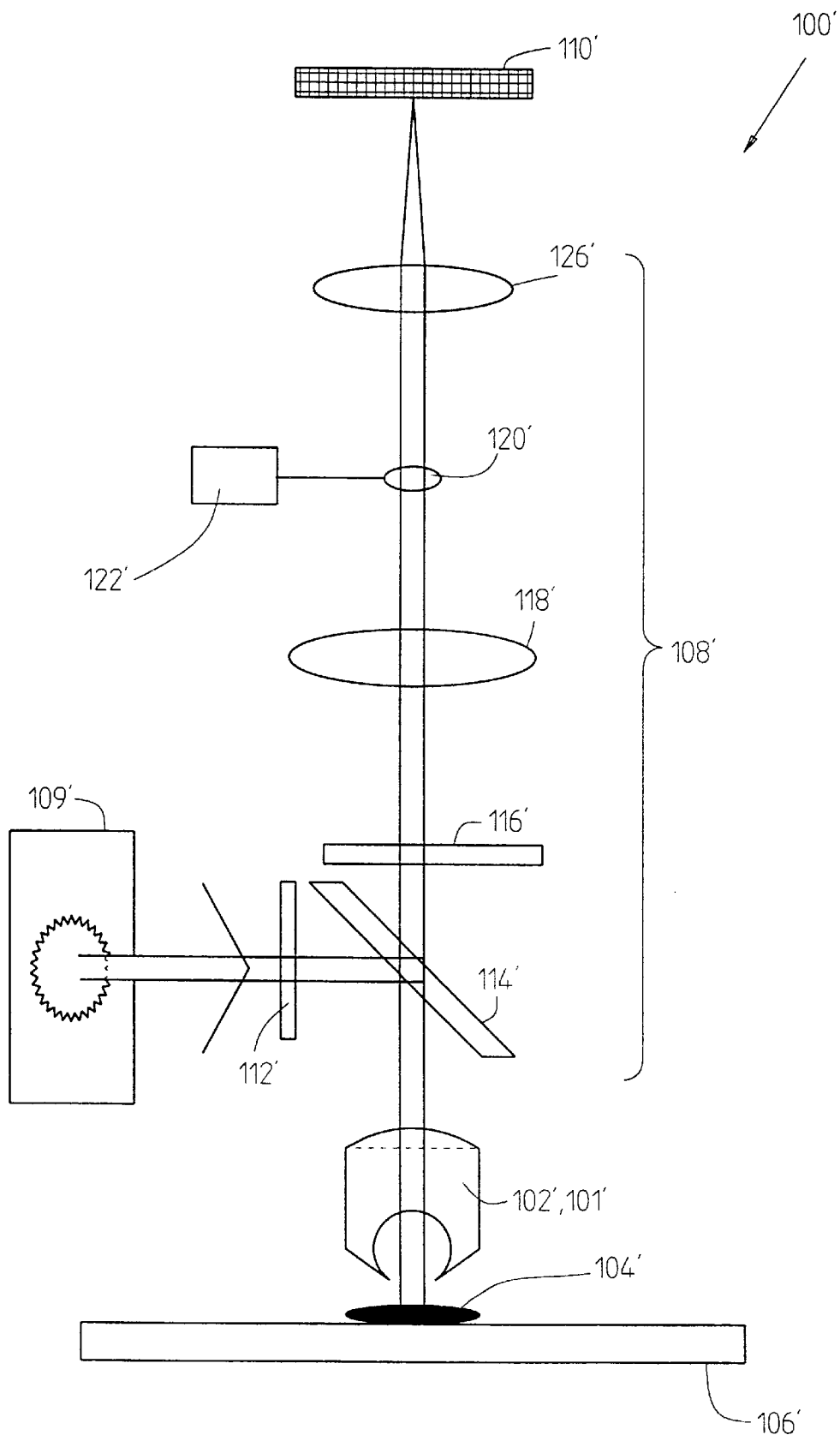
FIG. 11 is a schematic depiction of a tunable filter including spectral decorrelation measurement apparatus according to the present invention.

With reference now to FIG. 11. For ease of measurement, a tunable filter to serve as the decorrelation matched filters is placed in an apparatus which is referred to hereinbelow as a spectral decorrelation measurement apparatus, or apparatus 100'. Apparatus 100' is connected to a microscope 101', which is indicated by its objective lens 102'. A sample of in situ painted chromosomes 104' to be analyzed is placed under microscope 101', on a supporting plane 106'. Apparatus 100' further includes an optical system 108', which is for transmitting excitation light from light source 109' to sample 104' and emission light from sample 104' onto a detector 110', typically a two dimensional CCD array.

In a preferred embodiment, optical system 108' includes an excitation filter 112', which is placed in the path of light emitted from light source 109'. Excitation filter 112' is capable of transmitting light in the range required for excitation of the fluorophores in sample 104', e.g., in the ultraviolet and blue ranges, and of blocking light in the range of fluorescent emission. Optical system 108' further includes a dichroic filter 114', typically a triple dichroic filter, for directing exiting light from filter 112' to sample 104' and emission light from sample 104' to detector 110'. Preferably, optical system 108' further includes a barrier filter 116' for blocking any residual photons which are not in the spectral range of the emitted fluorescence. Depending on the type of microscope 101' employed, optical system 108' may further include a collimating lens 118' to ensure full collimation of the light. However, as well known in the art, some microscopes include a collimating lens themselves. In these cases collimating lens 118' may be discarded.

Optical system 108' further includes a tunable filter 120' and a tuning device 122'. Tuning device 122' is for sequentially tuning filter 120' according to precalculated tuning information to sequentially implement N (N is an integer greater than two, preferably N is in the range of 3–5) decorrelating matched filters as described above under Example 7. Device 122' preferably also includes tuning information to transform filter 120' into a transparent optical element through which light passes undisturbed. The number N of implemented decorrelating matched filters may vary as described above and is determined by the number of eigenvalues or PCs employed to construct the reference vector for each of the chromosomes, or, in other words, the reference template.

Optical system 108' further includes a focusing lens for focusing light after passage through filter 120' onto detector 110'.

The operation of apparatus 100 is as follows. Tunable filter 120' is sequentially tuned by tuning device 122' according to a precalculated set of information, as described above, to sequentially implement the N decorrelating matched filters, such that at selected times a different decorrelating matched filter is implemented, while detector 110' builds an images for each until one image for each implementation has been measured. One additional image is formed while filter 120' is tuned such that light passes therethrough is undisturbed, or without filter 120' altogether.

Using the data thus collected, Equation 9 above and the data in tables 4 and 6, the coordinates of the P N-dimension vector for each pixel are calculated in the N-dimensional space of the N PCs. These coordinates are then used for classification by employing the pre-prepared reference template, similarly to as described above under classification. As before, for color presentation, pixels attributed to each of the 24 different chromosome types are given a different artificial color to yield a 24 color karyotype.

It will be appreciated by one ordinarily skilled in the art that using apparatus 100' according to the present invention is benefactory for all the cytogenetic applications based on the classification approach of the present invention as delineated under Example 6 above, especially for chromosome banding analysis.

The apparatus of the present example has advantages over the apparatus of Example 9 in two respects. First, the apparatus according to this example has no moving parts. Second, the apparatus according to this Example is less "dedicated". That is to say, should a different experimental procedure employed for chromosome painting or banding, a new set of information is calculated to permit the tunable filter to implement a different set of decorrelation matched filters, suitable for data collection from the chromosomes according to the methods of the present invention and as detailed above. The operation of the apparatus of the present Example is highly suitable for computer control, which can control the operation of tuning device 122'. Therefore, a single apparatus can be made suitable for classification and analysis of painted and banded chromosomes painted or banded by various experimental procedures, simply by employing a matching software which includes an appropriate set of information for controlling the operation of device 122', and therefore of tunable filter 120'.

While the invention has been described with respect to a limited number of embodiments, it will be appreciated that many variations, modifications and other applications of the invention may be made.

What is claimed is:

1. A set of filters comprising N decorrelation matched filters for chromosome classification, said N decorrelation matched filters being dedicated for extracting decorrelated variables from chromosome samples combinatorially painted with fluorophores according to a specific experimental protocol, said N decorrelation matched filters being for decomposing spectral data into said decorrelated variables while simultaneously averaging over correlated spectral variables spanning a spectral range of a spectral measurement of said fluorophores, wherein N is an integer greater than 2 and further wherein a combined transmission spectrum of said N decorrelation matched filters spans said spectral range.

2. A spectral decorrelation measurement apparatus for chromosome classification by extracting decorrelated spectral data from chromosome samples combinatorially painted with fluorophores according to a specific experimental protocol, the apparatus is connected to a microscope used to view the samples, said apparatus comprising:

(a) a light source;

(b) a detector; and (c) an optical system for transmitting excitation light from said light source onto said samples and emission light from said samples onto said detector, said optical system including a set of N decorrelating matched filters, said N decorrelation matched filters being dedicated for extracting decorrelated variables from the chromosome samples painted according to the specific experimental protocol, said set of N decorrelation matched filters being for decomposing spectral data into said decorrelated variables while simultaneously averaging over correlated spectral variables spanning a spectral range of a spectral measurement of said fluorophores, wherein N is an integer greater than 2 and further wherein a combined transmission spectrum of said N decorrelation matched filters spans said spectral range.

3. A spectral decorrelation measurement apparatus for chromosome classification as in claim 2, wherein said optical system further includes:

(i) an excitation filter placed in the path of light emitted from said light source for transmitting light in the range required for excitation of fluorophores contained in the sample and for blocking light in the range of emission;

(ii) a dichroic filter for directing exiting light from said filter to the sample and emission light from said sample to said detector; and (iii) a focusing lens for focusing emitted light onto said detector.

4. A spectral decorrelation measurement apparatus for chromosome classification as in claim 3, wherein said optical system further includes:

(iv) a barrier filter for blocking any residual photons which are not in the spectral range of emission.

5. A spectral decorrelation measurement apparatus for chromosome classification as in claim 3, wherein said optical system further includes:

(iv) a collimating lens for collimating light reaching to any of said decorrelating matched filters.

6. A spectral decorrelation measurement apparatus for chromosome classification as in claim 2, wherein said decorrelation matched filters are arranged on a rotatable filter carrying element.

7. A spectral decorrelation measurement apparatus for chromosome classification by extracting decorrelated variables from chromosome samples combinatorially painted with fluorophores according to a specific experimental protocol, the apparatus is connected to a microscope used to view the sample, said apparatus comprising:

(a) a light source;

(b) a detector; and (c) an optical system for transmitting excitation light from said light source onto said samples and emission light from said samples onto said detector, said optical system including a tunable filter and a tuning device, said tuning device being for tuning said tunable filter to sequentially implement a set of N decorrelating matched filters, said sequentially implemented N decorrelation matched filters being dedicated for extracting decorrelated variables from the chromosome samples painted according to the specific experimental protocol, said ting of said tunable filter being for decomposing spectral data into said decorrelated variables while simultaneously averaging over correlated spectral variables spanning a spectral range of a spectral measurement of said fluorophores, wherein N is an integer greater than 2 and further wherein a combined transmission spectrum of said N decorrelation matched filters spans said spectral range.

8. A set of filters comprising N decorrelation matched filters for chromosome banding analysis, said N decorrelation matched filters being dedicated for extracting decorrelated variables from chromosome samples combinatorially painted with fluorophores according to a specific experimental banding protocol, said N decorrelation matched filters being for decomposing spectral data into said decorrelated variables while simultaneously averaging over correlated spectral variables spanning a spectral range of a spectral measurement of said fluorophores, wherein N is an integer greater than 2 and further wherein a combined transmission spectrum of said N decorrelation matched filters spans said spectral range.

9. A spectral decorrelation measurement apparatus for chromosome banding analysis by extracting decorrelated variables from a chromosome samples combinatorially painted with fluorophores according to a specific experimental banding protocol, the apparatus is connected to a microscope used to view the sample, said apparatus comprising:

(a) a light source;

(b) a detector; and (c) an optical system for transmitting excitation light from said light source onto said samples and emission light from said samples onto said detector, said optical system including a set of N decorrelating matched filters, said N decorrelation matched filters being dedicated for extracting decorrelated variables from the chromosome samples painted according to the specific experimental banding protocol, said N decorrelation matched filters being for decomposing spectral data into said decorrelated variables while simultaneously averaging over correlated spectral variables spanning a spectral range of a spectral measurement of said fluorophores, wherein N is an integer greater than 2 and further wherein a combined transmission spectrum of said N decorrelation matched filters spans said spectral range.

10. A spectral decorrelation measurement apparatus for chromosome banding analysis as in claim 9, wherein said optical system further includes:

(i) an excitation filter placed in the path of light emitted from said light source for transmitting light in the range required for excitation of fluorophores contained in the sample and for blocking light in the range of emission;

(ii) a dichroic filter for directing exiting light from said filter to the sample and emission light from said sample to said detector; and (iii) a focusing lens for focusing emitted light onto said detector.

11. A spectral decorrelation measurement apparatus for chromosome banding analysis as in claim 10, wherein said optical system further includes:

(iv) a barrier filter for blocking any residual photons which are not in the spectral range of emission.

12. A spectral decorrelation measurement apparatus for chromosome banding analysis as in claim 10, wherein said optical system further includes:

(iv) a collimating lens for collimating light reaching to any of said decorrelating matched filters.

13. A spectral decorrelation measurement apparatus for chromosome banding analysis as in claim 9, wherein said decorrelation matched filters are arranged on a rotatable filter carrying element.

14. A spectral decorrelation measurement apparatus for chromosome banding analysis by extracting decorrelated variables from a chromosome samples combinatorially painted with fluorophores according to a specific experimental banding protocol, the apparatus is connected to a microscope used to view the sample, said apparatus comprising:

(a) a light source;

(b) a detector; and (c) an optical system for transmitting excitation light from said light source onto said samples and emission light from said samples onto said detector, said optical system including a tunable filter and a tuning device, said tuning device being for tuning said tunable filter to sequentially implement a set of N decorrelating matched filters, said sequentially implemented N decorrelation matched filters being dedicated for extracting decorrelated variables from the chromosome samples painted according to the specific experimental protocol, said tuning of said tunable filter being for decomposing spectral data into said decorrelated variables while simultaneously averaging over correlated spectral variables spanning a spectral range of a spectral measurement of said fluorophores, wherein N is an integer greater than 2 and further wherein a combined transmission spectrum of said N decorrelation matched filters spans said spectral range.

* * * * *

UNITED STATES PATENT AND TRADEMARK OFFICE
CERTIFICATE OF CORRECTION

PATENT NO. : 5,912,165
DATED : June 15, 1999
INVENTOR(S) : Cabib et al.

It is certified that error appears in the above-identified patent and that said Letters Patent is hereby corrected as shown below:

Title page,
Item [54], Title should be changed from:
"METHOD FOR CHROMOSOME CLASSIFICATION BY DECORRELAITON STATISTICAL ANALYSIS AND HARDWARE THEREFORE"

to read:

-- METHOD FOR CHROMOSOME CLASSIFICATION BY DECORRELATION STATISTICAL ANALYSIS AND HARDWARE THEREFORE --

Signed and Sealed this

Twenty-sixth Day of February, 2002

Attest:

JAMES E. ROGAN
*Attesting Officer*  *Director of the United States Patent and Trademark Office*